(12) United States Patent
Ondrla et al.

(10) Patent No.: US 7,198,628 B2
(45) Date of Patent: Apr. 3, 2007

(54) ADJUSTABLE HUMERAL CUTTING GUIDE

(75) Inventors: Jeffrey M. Ondrla, Leesburg, IN (US);
Andrea Hahn, Petersburg, MI (US);
Gerald Ross Williams, Jr., Villanova, PA (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/881,795

(22) Filed: Jun. 30, 2004

(65) Prior Publication Data

US 2006/0004373 A1 Jan. 5, 2006

(51) Int. Cl.
*A61B 17/15* (2006.01)
(52) U.S. Cl. .................................................. 606/87
(58) Field of Classification Search .............. 606/86–89
See application file for complete search history.

(56) References Cited

U.S. PATENT DOCUMENTS

| | | | | |
|---|---|---|---|---|
| 4,736,737 A | * | 4/1988 | Fargie et al. .................. | 606/88 |
| 5,108,396 A | | 4/1992 | Lackey et al. | |
| 5,464,406 A | * | 11/1995 | Ritter et al. ................... | 606/86 |
| 5,474,559 A | * | 12/1995 | Bertin et al. ................... | 606/89 |
| 5,484,446 A | * | 1/1996 | Burke et al. ................... | 606/87 |
| 5,628,750 A | * | 5/1997 | Whitlock et al. .............. | 606/88 |
| 5,688,284 A | * | 11/1997 | Chervitz et al. ............... | 606/96 |
| 5,830,216 A | * | 11/1998 | Insall et al. .................... | 606/88 |
| 5,961,555 A | | 10/1999 | Huebner | |
| 6,102,953 A | | 8/2000 | Huebner | |
| 6,168,627 B1 | | 1/2001 | Huebner | |
| 6,168,628 B1 | | 1/2001 | Huebner | |
| 6,193,758 B1 | | 2/2001 | Huebner | |
| 6,494,913 B1 | | 12/2002 | Huebner | |
| 6,503,255 B1 | * | 1/2003 | Albrektsson et al. .......... | 606/89 |
| 6,685,711 B2 | * | 2/2004 | Axelson et al. ................ | 606/88 |
| 6,712,823 B2 | | 3/2004 | Grusin et al. | |
| 2002/0099381 A1 | * | 7/2002 | Maroney ....................... | 606/86 |
| 2004/0122436 A1 | * | 6/2004 | Grimm .......................... | 606/87 |
| 2004/0153083 A1 | * | 8/2004 | Nemec et al. ................. | 606/86 |
| 2004/0153084 A1 | * | 8/2004 | Haney et al. .................. | 606/87 |

* cited by examiner

*Primary Examiner*—Eduardo C Robert
*Assistant Examiner*—Richard Shaffer
(74) *Attorney, Agent, or Firm*—Maginot, Moore & Beck

(57) ABSTRACT

An adjustable humeral cutting guide for defining a cutting plane for a saw in a bone using a positioning structure includes a clamp, a saw guide, and an orientable coupling. The clamp is configured to be secured to the positioning structure. The saw guide includes a slot formed therein and formed to cooperate with a saw and limit the saw to cutting in a specific plane. The orientable coupling is mounted to the clamp and the saw guide. The orientable coupling is configured to adjust the saw guide at a selectable anterior/posterior angle and a selectable medial/lateral angle.

17 Claims, 19 Drawing Sheets

ADJUSTABLE HUMERAL CUTTING GUIDE

BACKGROUND AND SUMMARY

The invention relates to a cutting guide for bone preparation and more particularly to a cutting guide for preparing a bone for receipt of a stem of a prosthesis wherein the cutting guide is adjustable to facilitate cutting the bone in a plane that is adjustable anteriorly and posteriorly, laterally and medially, and in any combination thereof.

During shoulder arthroplasty, the humeral head must be resected to allow for the insertion of a humeral stem into the intramedullary canal of the humerus. The proximal end of the humerus includes the humeral head which articulates with the glenoid cavity of the shoulder in a ball and socket fashion. The humeral head is nearly hemispherical in form.

The prostheses typically used for shoulder arthroplasty include a stem portion designed to extend into the intramedullary canal of the humerus and a head portion designed to replace the humeral head. The head portion of the prosthesis extends angularly from the stem portion. The resection of the natural humeral head must be made so that the angle of the cut corresponds to the angle between the stem and head portions of the prosthesis. In addition, the rotation of the cut varies to adjust to bone wear or capsulor looseness.

There are eight essential variables relating to humeral arthroplasty. These include: the diameter of curvature of the prosthesis; the percentage of the sphere with this diameter that will be used as prosthetic articular surface; the superior/inferior position of the articular surface relative to the humerus; the anterior/posterior position of the articular surface relative to the humerus; the medial/lateral articular aspect of the articular surface with respect to the humerus; the anterior/posterior angulation (flexion/extension) of the articular surface relative to the prosthesis; the medial/lateral angulation (varus/valgus) of the prosthesis relative to the humerus; and, the rotational alignment of the prosthetic head with respect to the humeral axis. The goal of prosthetic arthroplasty is to duplicate the normal orientation of the humeral articular surface as well as its diameter of curvature and percentage of the sphere.

Many orthopaedic companies currently provide anatomically variable prosthesis with stems that facilitate adjusting the prosthesis to more accurately reflect the anatomy of the individual. For anatomically variable prostheses, most surgical techniques call for a "freehand" cut of the humeral head. Others have rudimentary guides that facilitate a planar cut but only allow for anterior/posterior (version) or medial/lateral adjustment of the cutting plane.

When the humeral head resection is made free hand, the elbow of the patient is flexed to 90° with the patient's forearm aimed at the midline of the operating surgeon's trunk. The humerus is externally rotated to provide the recommended degree of retrotorsion in relation to the axis of elbow motion. The resection is directed away from the surgeon, allowing the surgeon to reproduce the desired retrotorsion in the bone cut. A trial prosthesis may also be placed along the proximal humeral shaft as a guide for the proper inclination of the resection. The possibility for error exists with this free hand approach. Inaccurate resection can result in an ill-fitting prosthesis which may cause complications for the patient and may eventually require replacement of the prosthetic device.

Even when a cutting guide is utilized by the surgeon to ensure that the humeral head is resected along a plane of resection, the cutting guide places limits on the orientation of the plane of resection. The plane of resection includes both an anterior/posterior angle and a medial/lateral angle. Current humeral cutting guide designs only allow for the removal of the humeral head to be made at a selectable anterior/posterior angle or a set medial/lateral angle. Thus, the medial/lateral angle of the cutting plane cannot be adjusted in concert with the anterior/posterior angle with such cutting guides. Accordingly, the cut cannot be made along every potentially desired plane in three-dimensional space. Thus the surgeon has limited ability to make a cut that best matches the anatomy of each individual.

Many humeral cutting guides are adapted to clamp onto a reamer used to ream into the intramedullary canal prior to resection of the humeral head to provide a cavity into which a stem of a humeral prosthesis will be inserted. Following the reaming operation, the reamer is used as a temporary anchor for the cutting guide prior to adjustment of the angle of the cutting guide.

Accordingly, the need exists for a humeral cutting guide which will ensure an exact and precise resection of the humeral head. It would be desirable to have a cutting guide that allows for infinite variability of the cutting plane.

The disclosed humeral cutting guide allows for anterior/posterior and medial/lateral adjustment of the cutting plane to correspond to a humeral stem. The disclosed cutting guide is not only adjustable in the anterior/posterior direction, but also allows for the cut to be made in any direction in three-dimensional space. This gives the surgeon the opportunity to make a cut that can better match the anatomy of each individual.

The disclosed humeral cutting guide allows for the resection of the humeral head in any orientation in three-dimensional space. The guide locks on the reamer in a standard fashion. Additionally, the guide surface can be locked in an easily found zero position corresponding to a typical humeral head configuration.

According to one aspect of the disclosure, an adjustable humeral cutting guide for defining a cutting plane for a saw in a bone using a positioning structure is provided. The cutting guide includes a clamp, a saw guide, and an orientable coupling. The clamp is configured to be secured to the positioning structure. The saw guide includes a slot formed therein sized to receive a saw and limit the saw to cutting in a specific plane. The orientable coupling is mounted to the clamp and the saw guide. The orientable coupling is configured to adjust the saw guide at a selectable anterior/posterior angle and a selectable medial/lateral angle.

According to another aspect of the disclosure, an adjustable cutting guide for resection of a bone comprises a positioning structure, a clamp, a member, a saw guide and an orientable coupling. The positioning structure is configured to be at least temporarily fixed relative to the bone. The clamp is adapted to be coupled to the positioning structure for movement longitudinally with respect to a longitudinal axis of the bone and radially about the longitudinal axis of the bone. The member is coupled to the clamp for movement relative to the clamp in a direction transverse to the longitudinal axis of the bone. The saw guide defines a resection plane of reference for a saw received therein. The orientable coupling extends between the saw guide and member and facilitates adjustment of the resection plane of reference in three dimensions.

According to yet another aspect of the disclosure, an apparatus for guiding the resection of the head of a humerus comprises an intramedullary alignment member, an extramedullary alignment member, a translatable member, a saw guide and an orientable coupling. The intramedullary alignment member has a longitudinal axis and is structured for substantial axial alignment with the intramedullary canal of a humerus. The extramedullary alignment member extends substantially perpendicularly from the intramedullary alignment member and is translatable along, and rotatable about, the longitudinal axis of the intramedullary alignment member. The translatable member is translatable along the extramedullary alignment member. The orientable coupling extends between the saw guide and the translatable member and is configured to translate with respect to the translatable member in a direction transverse to the extramedullary alignment member. The orientable coupling is also configured to orient the saw guide in an orientation relative to the head of the humerus within a range desirable for humeral resection.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

In describing the disclosed device, reference will be made to the following figures in which.

Corresponding reference characters indicate corresponding parts throughout the several views. Like reference characters tend to indicate like parts throughout the several views.

DETAILED DESCRIPTION

Figure 1:
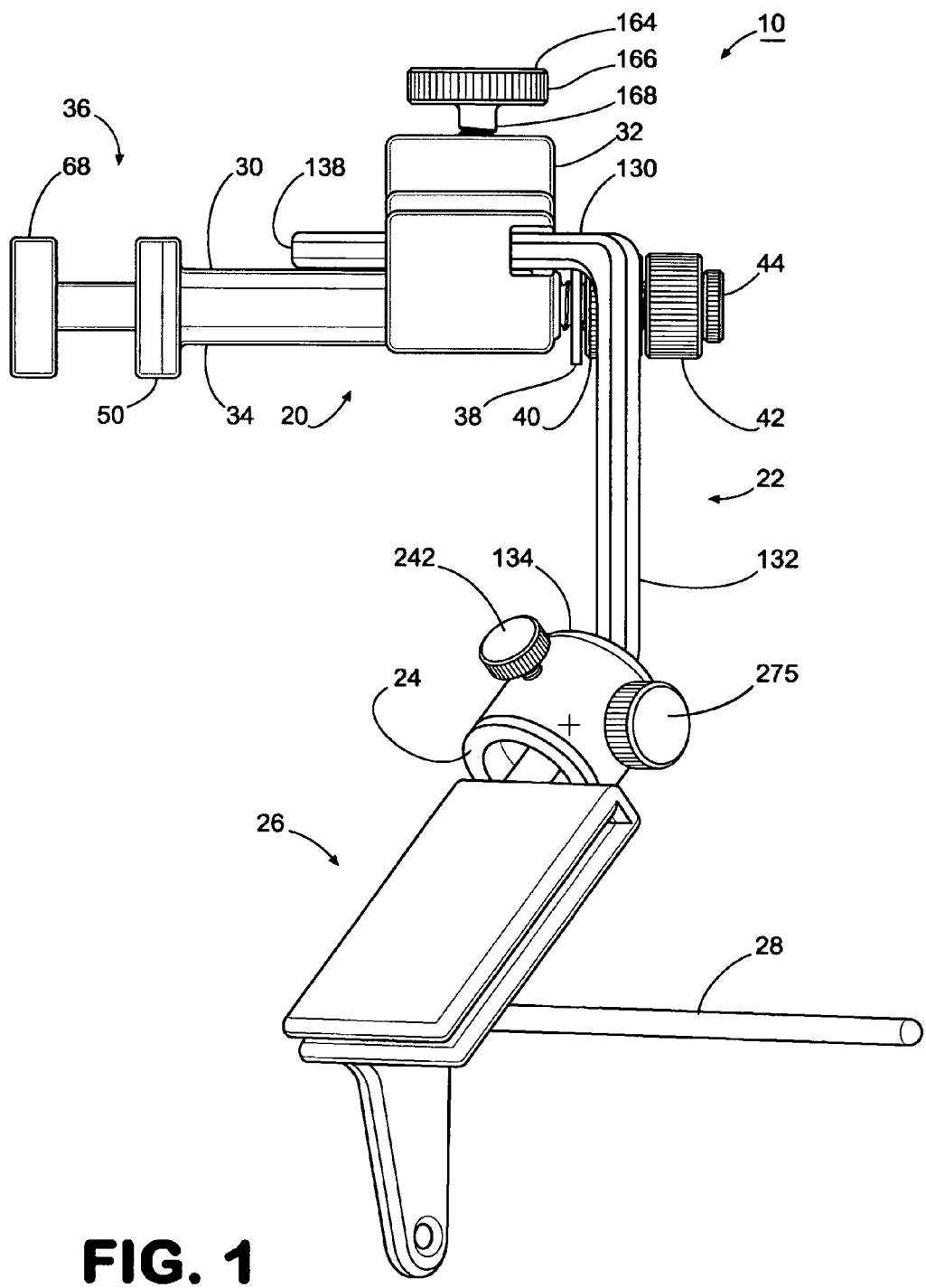
FIG. 1 is a perspective view of an adjustable humeral cutting guide including a reamer clamp assembly, an orientable holder, an orientable holder threaded cap, a saw guide and an alignment guide.
Figure 3:
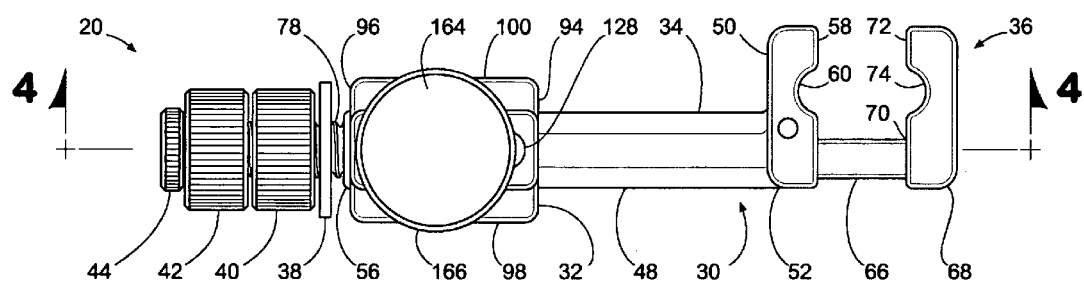
FIG. 3 is an elevation view of the reamer clamp assembly of FIG. 2 showing an orientable holder-mounting cavity in the sliding block within which a mounting arm of the orientable holder is slidably received.
Figure 2:
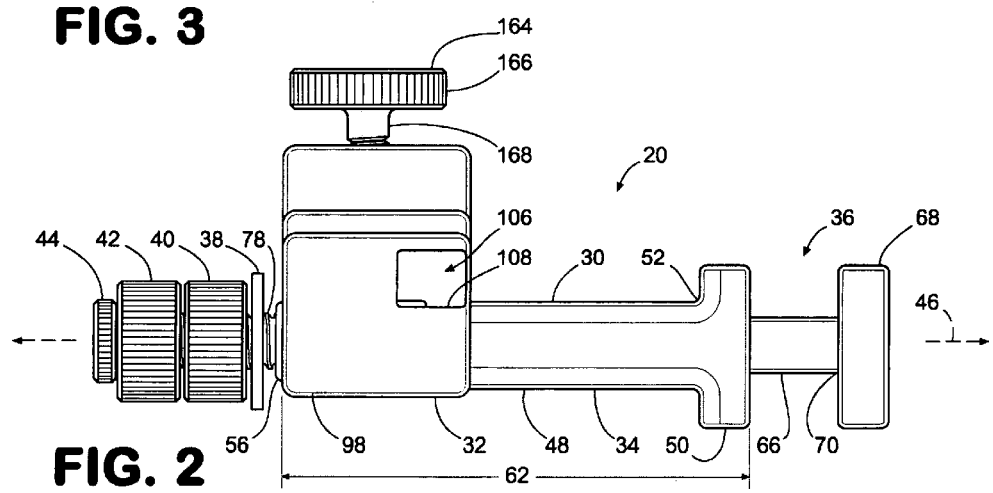
FIG. 2 is an elevation view of the reamer clamp assembly of FIG. 1 showing a reamer clamp with a clamp body having a first jaw and an end clamp assembly that includes a rod having a second jaw mounted to the first end and a threaded second end with the end clamp assembly mounted to the clamp body so that the second jaw is movable towards and away from the first jaw and can be locked in position with a washer, two lock nuts and an adjustable end cap, additionally, a sliding block is also shown mounted to the clamp body for translational movement along the clamp body.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The disclosed adjustable humeral cutting guide 10 allows for the resection of the humeral head 12 in any orientation in three-dimensional space. The adjustable humeral cutting guide 10 locks onto a reamer 14 received in the intramedullary canal of the humerus 16 in a standard fashion, as shown, for example, in FIGS. 30–32. Three-dimensional adjustment of the cutting plane can be obtained by loosening two set screws 242, 275 thereby allowing the cutting guide surface to be adjusted to the anatomy of the patient. Once the cutting guide 10 is adjusted, the set screws 242, 275 are tightened such that the cutting guide 10 is locked in place, as shown, for example, in FIGS. 31 and 32. Cutting can then be accomplished in the correct three-dimensional plane of the humeral head. Additionally, the guide surface can be locked in an easily found zero position corresponding to a typical humeral head configuration, as shown, for example, in FIG. 30.

The disclosed adjustable humeral cutting guide 10 comprises a reamer clamp assembly 20, an orientable holder 22, a threaded cap 24, a saw guide 26 and a removable alignment guide 28, as shown, for example, in FIG. 1. The reamer clamp assembly 20 attaches to both the reamer 14, or some other intramedullary alignment member or positioning structure, and the orientable holder 22. The reamer clamp assembly 20 can be adjusted vertically on the reamer 14, as shown, for example, in FIGS. 29–31, to adjust the entire adjustable humeral cutting guide 10 vertically with respect to the reamer 14 and the humerus 16.

As shown, for example, in FIGS. 1–8, the reamer clamp assembly 20 includes a reamer clamp 30 and a sliding block 32. The reamer clamp 30 includes a clamp body 34, an end clamp assembly 36, a washer 38, two locking nuts 40, 42 and an end cap 44. The clamp body 34 is formed about a longitudinal axis 46 and includes a hollow tube 48 coupled to a first jaw 50 at a first end 52. A rod-receiving lumen 54 extends longitudinally through the hollow tube 48 from the first end 52 to a second end 56. Illustratively, rod-receiving lumen 54 has a circular cross-section and is formed concentrically about the longitudinal axis 46. In the illustrated embodiment, the outer walls of hollow tube 48 form an octagon. The first jaw 50 extends from the first end 52 of the hollow tube 48 and is formed to included a reamer-engaging surface 58 having a reamer-receiving indentation 60 formed therein. The clamp body 34 has a length 62, which in the illustrated embodiment is 2.292 inches. The rod-receiving lumen 54 has an internal diameter 64 which in the illustrated embodiment is approximately 0.255 inches.

The end clamp assembly 36 includes a rod 66 and a second jaw 68. The second jaw 68 is coupled to the first end 70 of the rod 66 and extends laterally therefrom. The second jaw 68 is similar to the first jaw 50 and is designed to cooperate therewith to secure a reamer 14 between the jaws 50, 68 of the reamer clamp 30, as shown, for example, in FIGS. 28–32. Thus the second jaw 68 includes a reamer-engaging surface 72 with a reamer-receiving indentation 74 formed therein.

The rod 66 of end clamp assembly 36 has a diameter 76 slightly smaller than the inside diameter 64 of rod-receiving lumen 54 to facilitate rod 66 being received in rod-receiving lumen 54 for longitudinal movement therethrough. In the illustrated embodiment, the diameter 76 of the rod 66 is approximately 0.250 inches. An external thread 78 is formed on the outer surface of the rod 66 beginning at the second end 80 and extending toward the first end 70 for a distance 82. In the illustrated embodiment, distance 82 is approximately 1.125 inches. The external thread 78 is configured to mate and cooperate with an internal thread 84 formed in a first locking nut 40, an internal thread 86 formed in a second locking nut 42 and an internal thread 88 formed in an end cap 44.

The end clamp assembly 36 has a length 90 that is greater than the length 62 of the clamp body 34. In the illustrated embodiment, the length 90 of the end clamp assembly 36 is approximately 3.75 inches. Thus, when the rod 66 of the end clamp assembly 36 is received in the rod-receiving lumen 54 of the hollow tube 48, the second end 80 of the rod 66 extends beyond the second end 56 of the hollow tube 48 so that the washer 38, locking nuts 40, 42, and the end cap 44 can be received on the second end 80 of the rod 66 to retain the end clamp assembly 36 within clamp body 34. The second jaw 68 and first jaw 50 are disposed relative to each other so that the reamer-engaging surfaces 58, 72 are facing each other and the reamer-receiving indentations 60, 74 are located opposite to each other, as shown, for example, in FIG. 3.

The two locking nuts 40, 42 may be rotated on the threaded rod 66 to move the second jaw 68 linearly closer to and farther away from the first jaw 50. The first locking nut 40 engages the washer 38 which engages the second end 56 of the clamp body 34 to limit the outward movement of the end clamp assembly 36 with respect to the clamp body 34. The second locking nut 42, when tightened, engages the first locking nut 40 to lock both nuts 40, 42 in position to prevent loosening due to vibration. The reamer 14, received in the reamer-receiving indentations 60, 74 in the first jaw 50 and second jaw 68, cooperates with the first and second jaws 50, 68 to limit the inward movement of the end clamp assembly 36 with respect to the clamp body 34.

Figure 29:
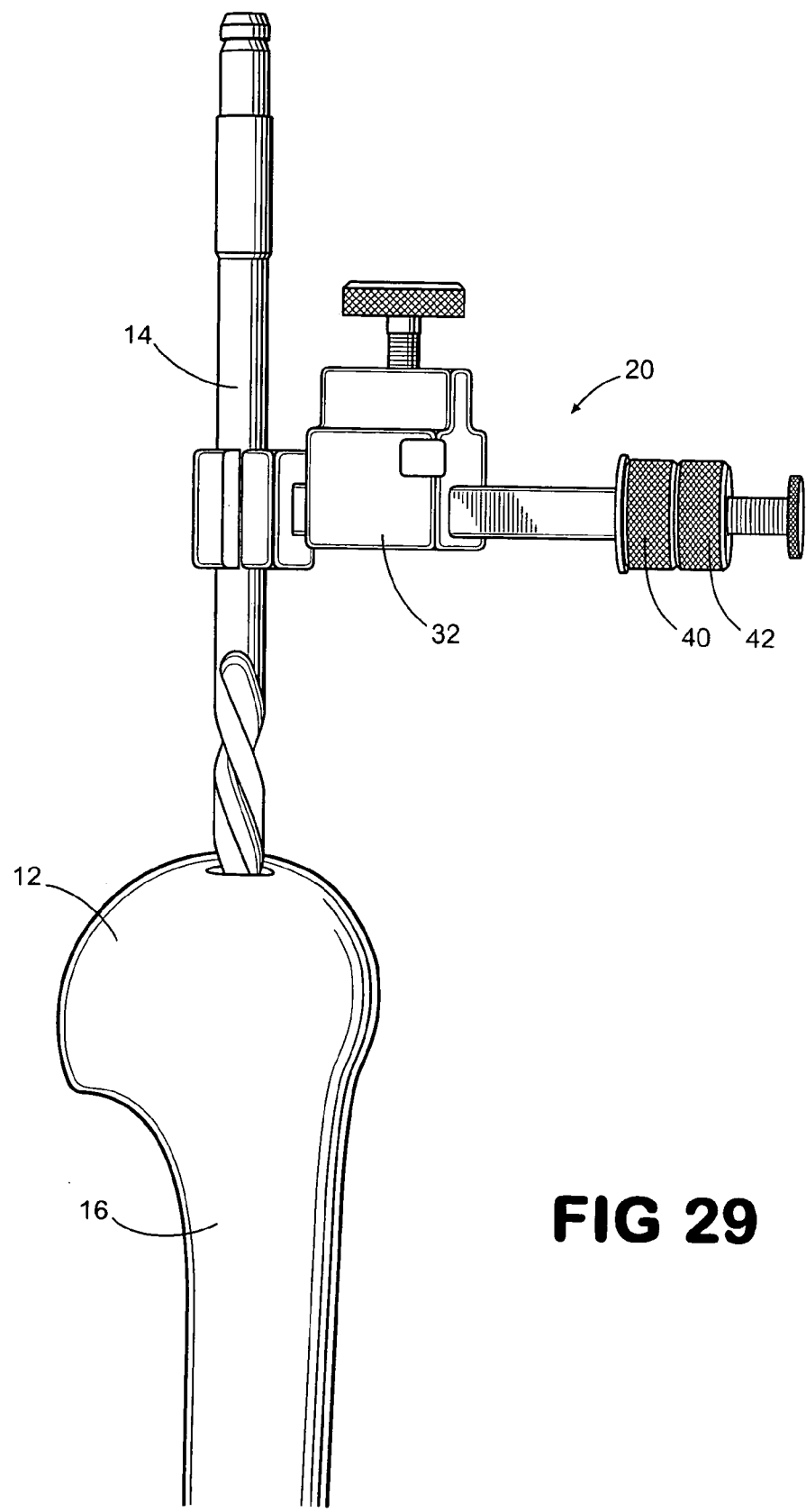
FIG. 29 is a perspective view similar to FIG. 28 showing the T-handle removed from, and a clamp portion of the adjustable humeral cutting guide attached at a first location to, the reamer with the sliding block positioned on the clamp body adjacent the humerus.

When the jaws 50, 68 reach the desired spacing, as for example when they are secured to the reamer 14, as shown, for example, in FIG. 29, the locking nuts 40, 42 may be tightened against the second end 56 and against each other to lock the jaws 50, 68 in place. Thus the reamer clamp 30 is locked onto the reamer 14 which is disposed in the intramedullary canal of the humerus 16. Prior to locking the jaws 50, 68 in place on the reamer 14, the reamer clamp 30 may be adjusted vertically along the reamer 14 and may be rotated about the reamer 14 to a desired position, as shown, for example, in comparing FIGS. 29 and 30. After this adjustment, the reamer clamp 30 is secured to the reamer 14 by tightening the two locking nuts 40, 42.

The sliding block 32 includes a front surface 94, a rear surface 96, a first side wall 98, a second side wall 100 and a top surface 102. Illustratively each side wall 98, 100 is parallel to the other and perpendicular to the front and rear surfaces 94, 96 and the top surface 102. The sliding block 32 is formed to include a clamp-receiving passage 92 extending therethrough from the front surface 94 to the rear surface 96 parallel to the side walls 98, 100 and the top surface 102, as shown, for example, in FIGS. 4, 5 and 8. As shown, for example, in FIGS. 1–3, the hollow tube 48 of the reamer clamp 30 has an external octagonal shape. The clamp-receiving passage 92 has an internal shape (FIG. 5) that conforms to the external shape of the surface of the hollow tube 48 so that the sliding block 32 can slide longitudinally along the clamp body 32 when the hollow tube 48 of the clamp body 32 is received in the clamp-receiving passage 92.

The sliding block 32 is also formed to include a mounting arm-receiving passage 106 therethrough extending between the side walls 98, 100. The mounting arm-receiving passage 106 is formed to extend at an angle 104 relative to the first side wall 98. In the illustrated embodiment, the angle 104 is approximately forty-five degrees. The bottom wall 108 of the mounting arm-receiving passage 106 is displaced from the top 102 of the sliding block 32 by a displacement 110 that is less than the displacement 112 of the top wall 114 of the clamp-receiving passage 92 from the top surface 102 of the sliding block 32. In the illustrated embodiment, the displacement 110 of the bottom wall 108 of the mounting arm-receiving passage 106 from the top surface 102 is approximately 0.75 inches and the displacement 112 of the top wall 114 of the clamp-receiving passage 96 from the top surface 102 is approximately 0.71 inches. Thus, the mounting arm-receiving passage 106 forms a junction 116 with the clamp-receiving passage 92, as shown, for example, in FIGS. 4 and 8.

A threaded set screw-receiving hole 118 is formed to extend between the top surface 102 of the sliding block 32 and the top wall 120 of the mounting arm-receiving passage 106. A ball spring hole 122 is formed to extend between the top surface 102 and the top wall 114 of the clamp-receiving passage 92. The ball spring hole 122 is positioned between, and is formed parallel to, the front wall 94 and the screw-receiving hole 118, as shown, for example, in FIGS. 4, 6 and 8. The ball spring hole 122 is formed to include an annular snap ring seat 124 adjacent the top surface 102 to receive a snap ring 126 securing a ball spring assembly 128 within the hole 122. One ball of the ball spring assembly 128 engages the hollow tube 48 of the clamp body 32 to facilitate sliding of the clamp body 32 within the clamp-receiving passage 92.

As shown, for example, in FIGS. 1, 9–11, the orientable holder 22 is formed to include a mounting arm 130, an offset arm 132 and a socket 134. The mounting arm 132 is formed symmetrically about an axis 136 and has a free end 138 and an end 140 coupled to one end 142 of the offset arm 132. The offset arm 132 is formed symmetrically about an axis 144 and extends from the one end 142 to the socket end 146 that is mounted to the socket 134. Both the mounting arm 130 and the offset arm 132 have an octagonal cross section. In the illustrated embodiment the axis 136 is perpendicular to the axis 144.

Illustratively, the socket 134 includes an axis 148, a circular end wall 150 formed perpendicular to the axis 148, a cylindrical side wall 152 formed concentrically about the axis 148 and a mounting end 154 formed to include a cavity 156 formed symmetrically about the axis 148. The cavity 156 extends inwardly from the mounting end 154 toward the end wall 150. The circular end wall 150 of the socket 134 is flat and lies in a plane 160 perpendicular to the axis 148. The axis 148 of the socket 134 forms an angle 162 with the axis 144 of the offset arm 132 in the plane of the paper in FIG. 10. The axis 148 of the socket 134 and the axis 144 of the offset arm 132 both lie in a plane parallel to the paper in FIG. 10.

Figure 4:
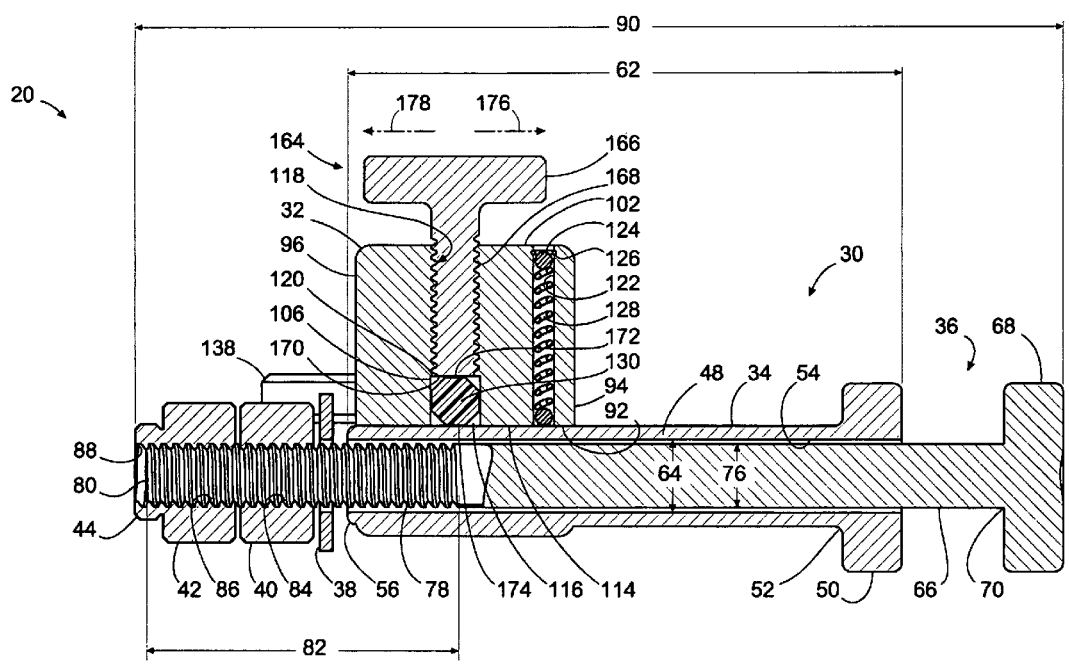
FIG. 4 is a sectional view taken along line 4—4 of the reamer clamp assembly of FIG. 3 shown with a portion of the mounting arm of the orientable holder received in the orientable holder-mounting cavity.
Figure 5:
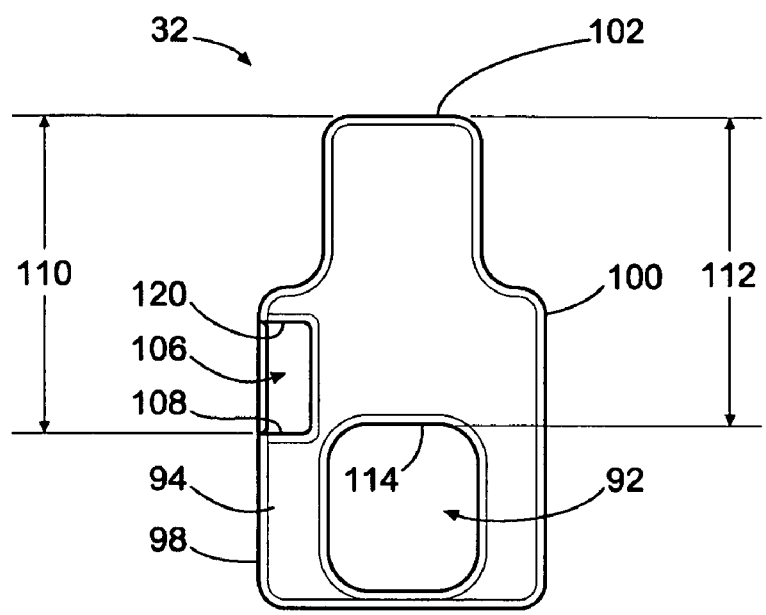
FIG. 5 is an elevation view of the sliding block of FIG. 2 showing the reamer clamp body-receiving cavity extending laterally through the sliding block and one opening of the orientable holder-mounting cavity on the left side of the sliding block.
Figure 6:
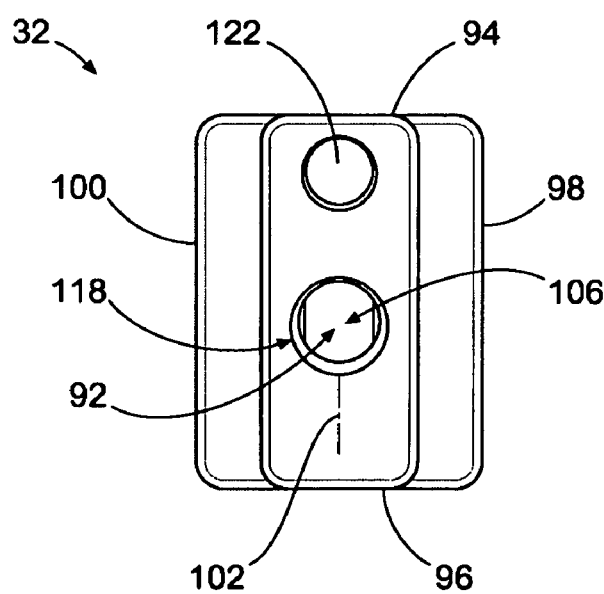
FIG. 6 is a plan view of the sliding block of FIG. 11.
Figure 7:
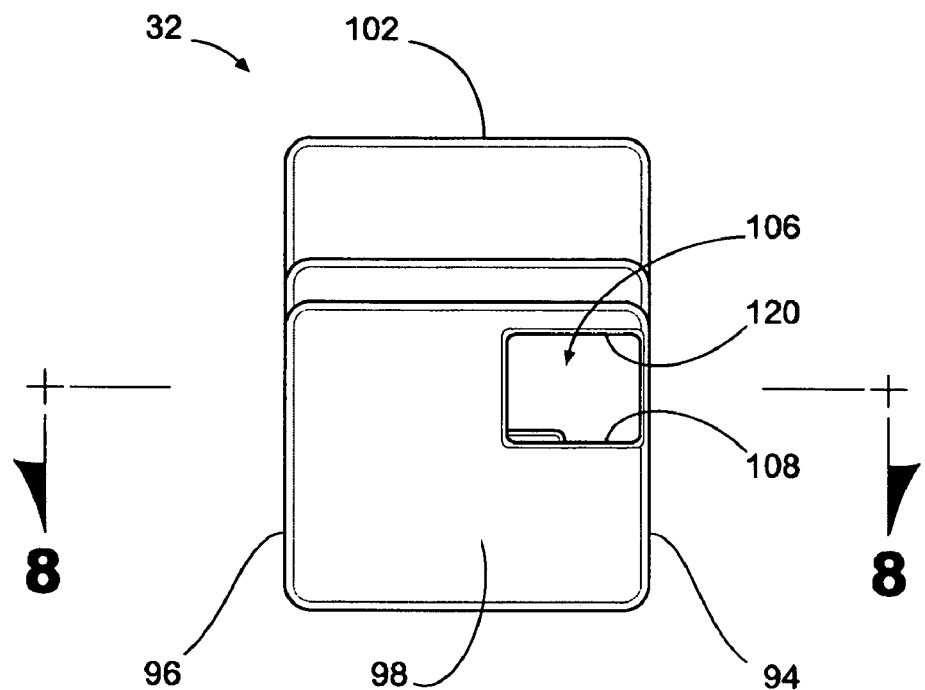
FIG. 7 is an elevation view of the sliding block of FIG. 5 showing one opening of the orientable holder-mounting cavity.
Figure 8:
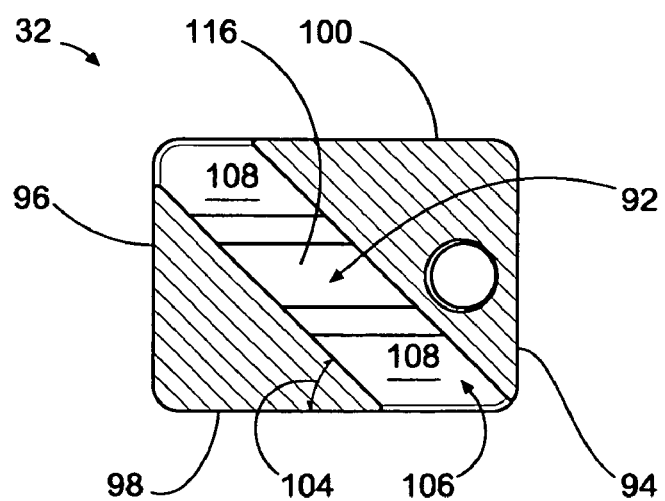
FIG. 8 is a sectional view of the sliding block taken along line 8—8 of FIG. 7 showing the orientable holder-mounting cavity within which the mounting arm of the orientable holder is slidably received and the intersection with the reamer clamp body-receiving cavity.
Figure 9:
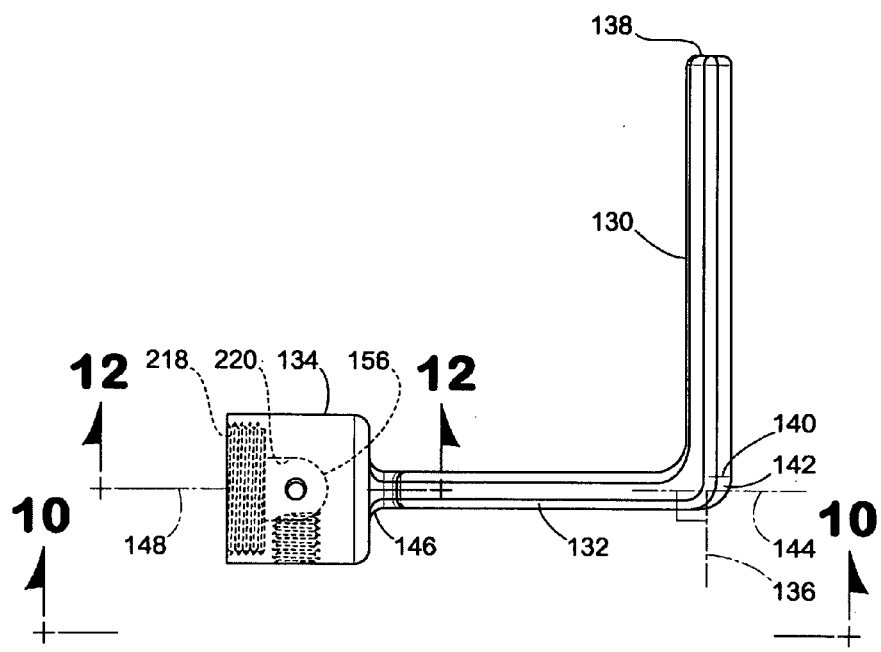
FIG. 9 is an elevation view of the orientable holder of FIG. 1 showing a mounting arm, an offset arm and a socket.
Figure 10:
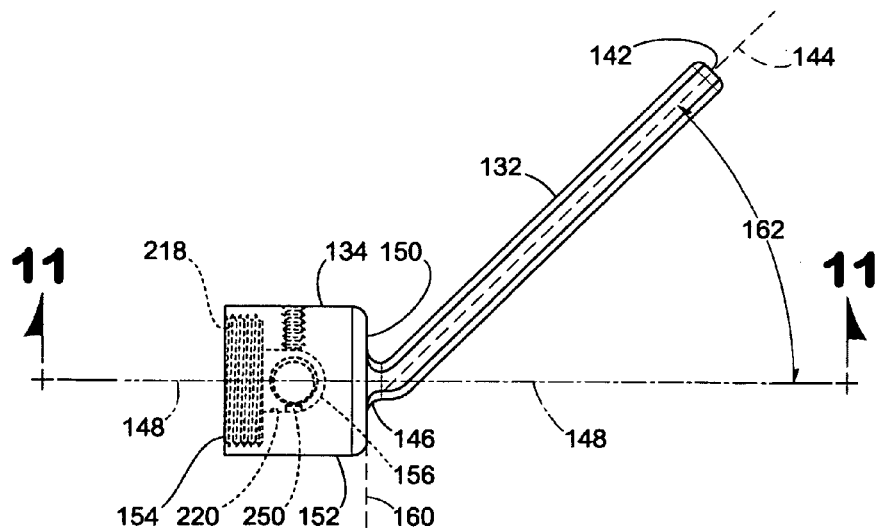
FIG. 10 is an elevation view taken along line 10—10 of the orientable holder of FIG. 9.
Figure 11:
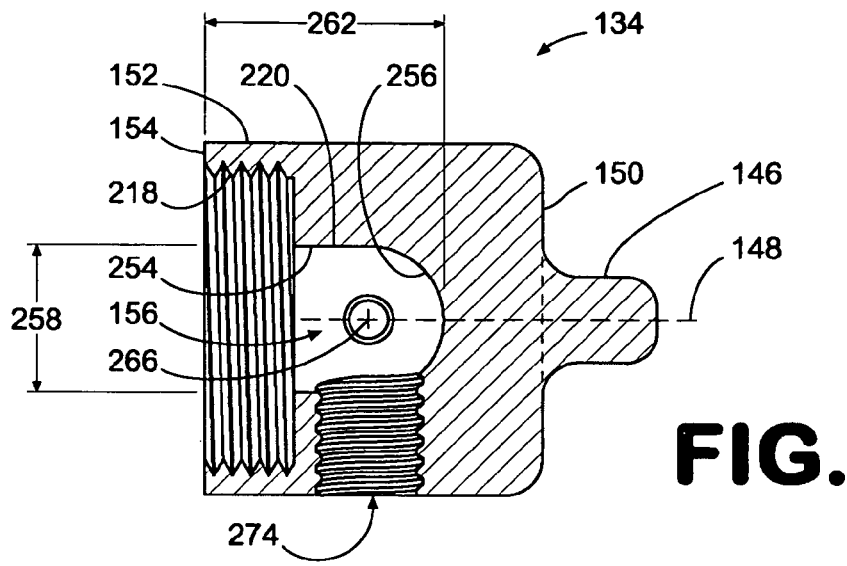
FIG. 11 is a sectional view of taken along line 11—11 of the orientable holder of FIG. 10 showing the socket and offset arm.
Figure 12:
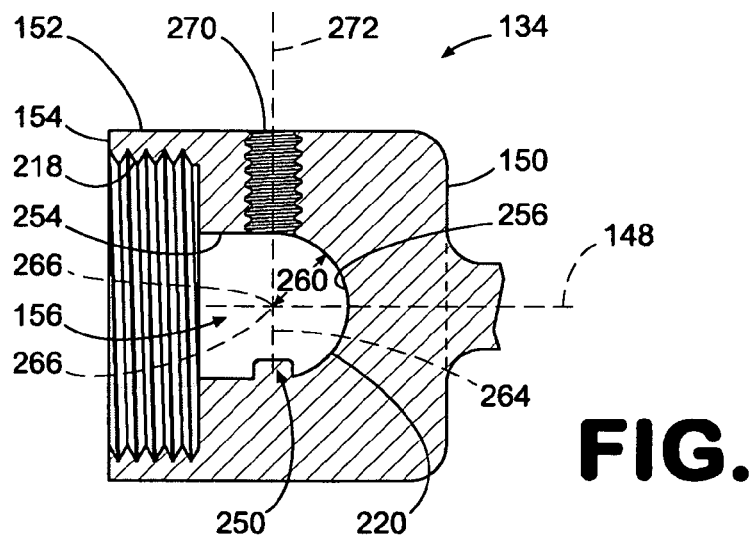
FIG. 12 is a sectional view taken along line 12—12 of the socket of FIG. 9 showing the limiter peg and zero positioning screw threaded hole.
Figure 13:
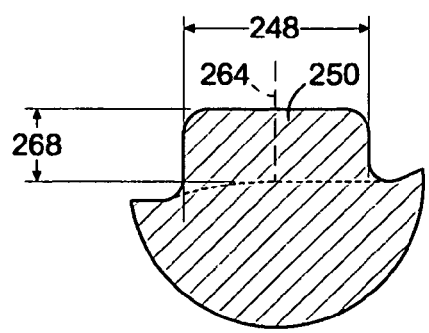
FIG. 13 is a detailed view of the limiter peg of FIG. 12.
Figure 14:
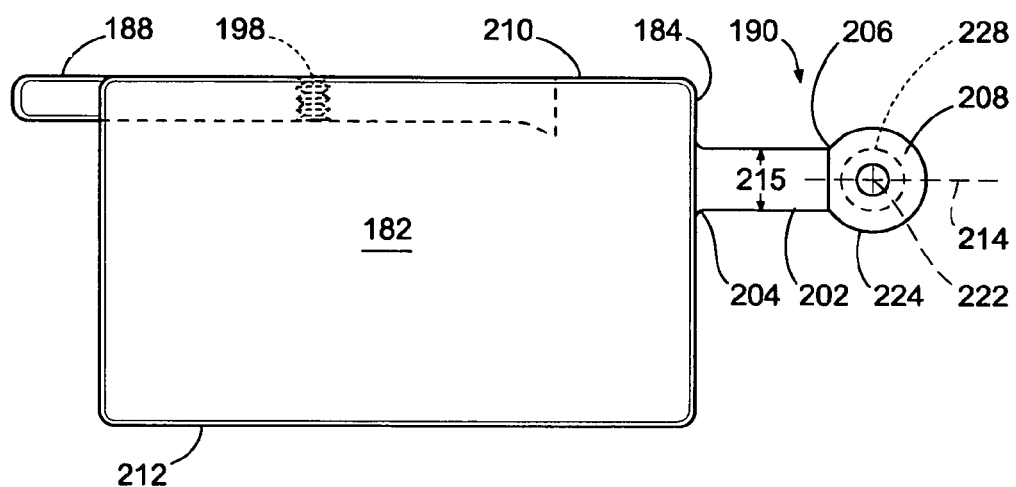
FIG. 14 is a plan view of the saw guide of FIG. 1 showing a guide plate with a mounting plate extending into the paper and a coupling arm extending to the right, the coupling arm includes a shaft mounted to the guide plates at one end and a mounting ball on the other end, the mounting ball is formed to include a cavity within which the end of a zero positioning set screw is received.
Figure 15:
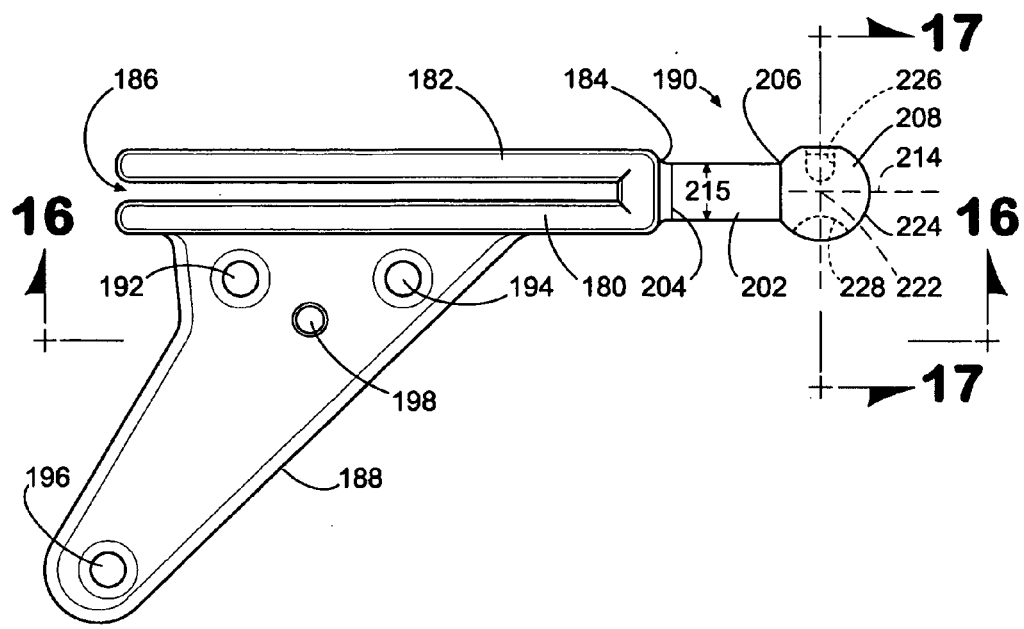
FIG. 15 is an elevation view of the saw guide of FIG. 14 showing the two spaced apart saw guide plates, the mounting plate and the coupling arm showing the tang-receiving cavity and a zero positioning screw-receiving cavity formed in the ball in phantom lines.
Figure 16:
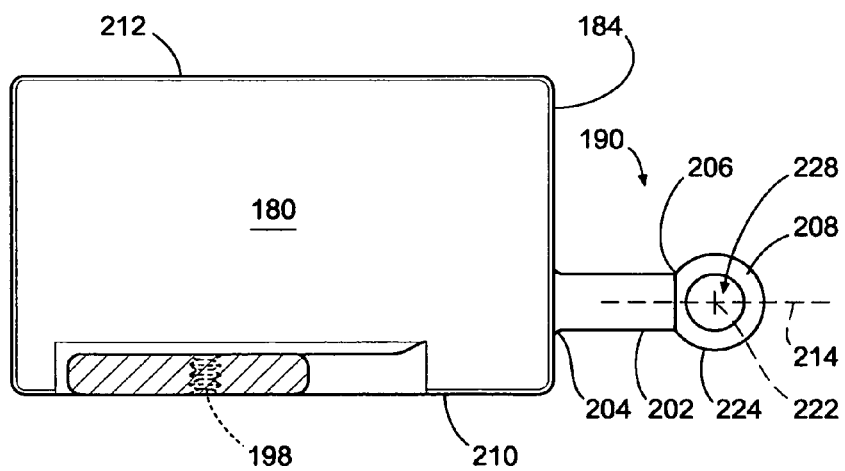
FIG. 16 is a sectional view taken along line 16—16 of the saw guide of FIG. 15 showing the zero positioning screw-receiving cavity formed in the ball and a threaded alignment guide receiving hole.
Figure 17:
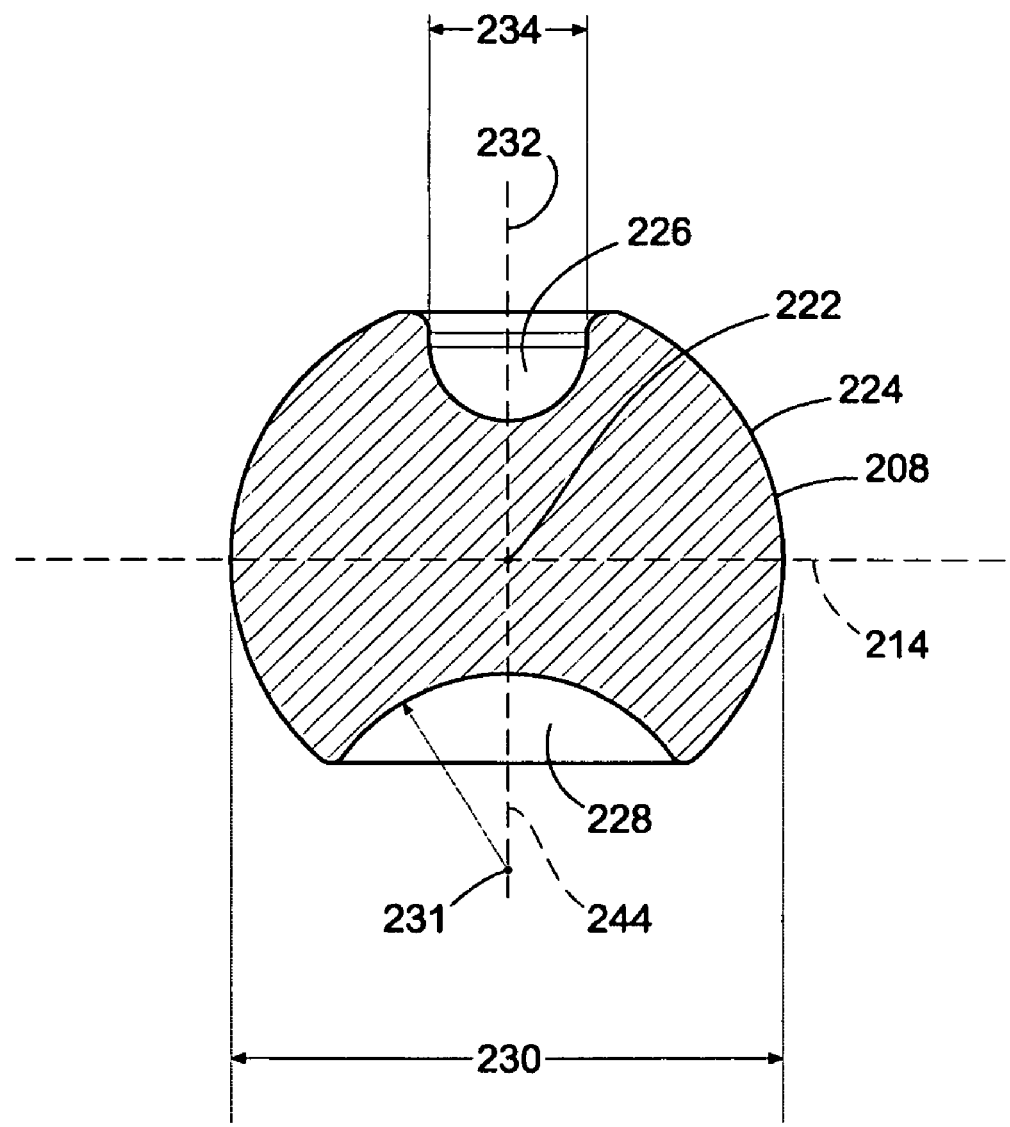
FIG. 17 is a sectional view taken along line 17—17 of the ball of the coupling arm of FIG. 15 showing the tang-receiving cavity and a zero positioning screw-receiving cavity.
Figure 18:
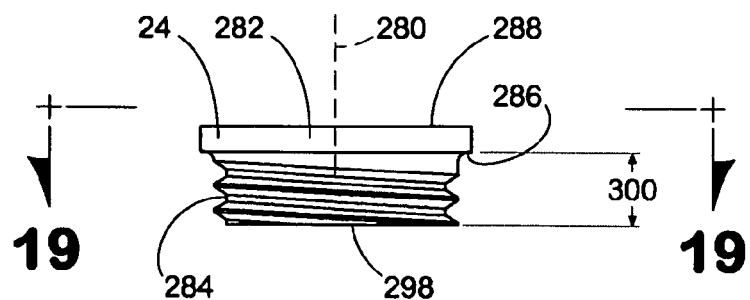
FIG. 18 is an elevation view of the slotted end cap of FIG. 1 showing the threads formed on the end opposite the head.
Figure 19:
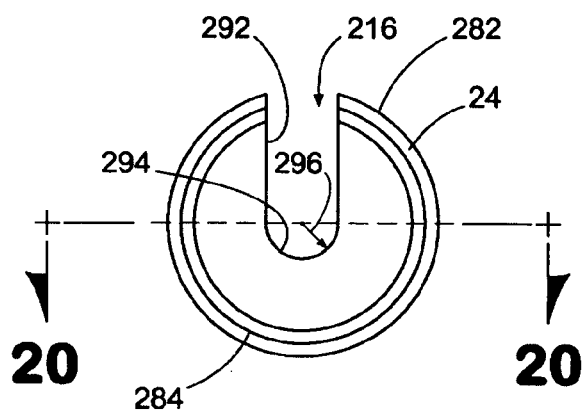
FIG. 19 is an elevation view taken along line 19—19 of the slotted end cap of FIG. 18 showing a slot formed in the head and one side of the threaded end into which the shaft of the coupling arm of the saw guide is received.
Figure 20:
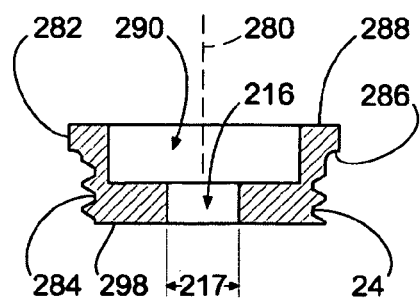
FIG. 20 is a sectional view taken along line 20—20 of the slotted end cap of FIG. 19.
Figure 21:
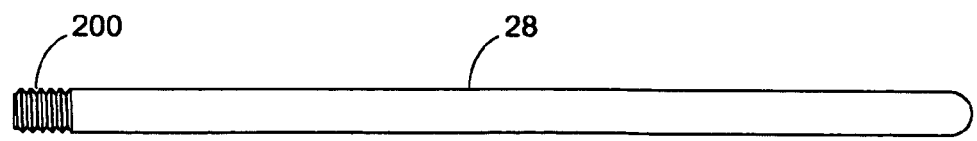
FIG. 21 is an elevation view of the alignment guide showing threads formed on one end of the alignment guide to facilitate temporarily coupling the alignment guide to the mounting plate of the saw guide.
Figure 22:
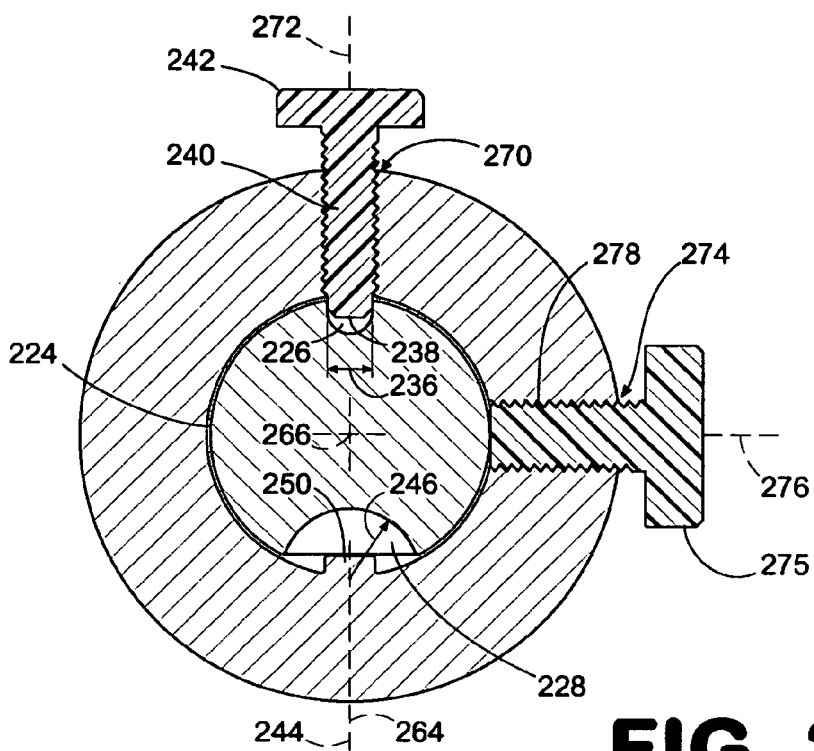
FIG. 22 is a sectional view taken through the plane of the axes of the zero positioning set screw and the orientation set screw of the mounting ball received in the cavity formed in the socket in a zero position established by the end of the shaft of the zero positioning set screw being received in the zero positioning cavity formed in the mounting ball.

The mounting arm 130 of the orientable holder 22 is configured to be received in the mounting arm-receiving passage 106 of the sliding block 32, as shown, for example, in FIGS. 1 and 4. The mounting arm 130 of the orientable holder 22 is removably mounted to the sliding block 36. The mounting arm 130 of the orientable holder 22 slides within the mounting arm-receiving passage 106 until it is locked in place by tightening the set screw 164, as shown, for example, in FIGS. 30 and 31. The set screw 164 includes a head 166, a threaded shaft 168 and an end 170. The threaded shaft 168 is configured to cooperate with the threaded set screw-receiving hole 118 to allow rotation of the set screw 164 to cause the end 170 of the set screw 164 to advance into and retract out of the screw-receiving hole 118.

When the set screw 164 is tightened, for example by the surgeon rotating the head 166 clockwise as seen from above, the end 170 of the set screw 164 engages one wall 172 of the mounting arm 130 and urges the oppositely facing wall 174 of the mounting arm 130 into engagement with the portion of the hollow tube 48 of the clamp body 32 that is positioned within the junction 116 of the clamp-receiving passage 92 and the mounting arm-receiving passage 106. Thus, tightening the set screw 164 locks the sliding block 32 in a position relative to the reamer clamp 30 and locks the orientable holder 22 in a position relative to the sliding block 32.

Prior to tightening the set screw 164, the sliding block 32 may slide along the hollow tube 48 of the reamer clamp 30 in the direction of the arrow 176 or the arrow 178 to allow for adjustment of the sliding block 32, the orientable holder 22 and the saw guide 26 in the horizontal direction. Prior to tightening the set screw 164, the mounting arm 130 of the orientable holder 22 slides within the mounting arm-receiving passage 106 of the sliding block 32 allowing for the orientable holder 22 and the saw guide 26 coupled thereto to be adjusted anteriorly/posteriorly. Once the set screw 164 is tightened, the orientable holder 22 and the saw guide 26 coupled thereto are locked into specific horizontal and anterior/posterior positions. However, the socket 134 of the orientable holder 22 and the mounting ball 208 of the saw guide 26 still permit adjustment of the orientation of the saw guide 26 as further described hereunder.

The saw guide 26 includes a plurality of spaced apart parallel guide plates 180, 182 coupled at one edge by an end wall 184 to define a captured saw blade slot 186, a mounting plate 188 and a coupling arm 190. The mounting plate 188 is coupled to the first guide plate 180 and extends perpendicularly therefrom. The mounting plate 188 is formed to include three pin-receiving holes 192, 194, 196 and a threaded alignment guide-receiving hole 198. Each of the three pin-receiving holes 192, 194, 196 is sized to receive a pin therethrough for pinning the saw guide 26 to the humerus 16, as shown, for example, in FIG. 31. The mounting plate 188 is contoured to match the contours of the humerus 16. The alignment guide-receiving hole 198 is sized and tapped to receive the externally threaded end 200 of the removable alignment guide 28 therein. The threaded alignment guide-receiving hole 198 is configured so that the removable alignment guide 28 attaches to the mounting plate 188 at a set degree of retroversion.

The coupling arm 190 is formed to include a shaft 202 mounted at one end 204 to the end wall 184 extending between the guide plates 180, 182 and mounted at the other end 206 to a mounting ball 208. The coupling arm 190 is mounted closer to the side 210 of the saw guide 26 to which the mounting plate 188 is mounted to the guide plate 180 than to the opposite side 212. The shaft 202 of the coupling arm 190 extends perpendicularly from the end wall 184 and is formed concentrically about an axis 214.

The coupling arm 190 has a diameter 215 sized to be received in the slot 216 of the slotted end cap 24. In the illustrated embodiment, the diameter 215 of the shaft 202 is approximately 0.15 inches while the width 217 of the slot 216 is approximately 0.23 inches. Thus, the slotted end cap 24 can be slid laterally onto the shaft 202 of the coupling arm 190 between the end wall 184 and the mounting ball 208 and then be screwed into the internally threaded bore 218 of the socket 134 to secure the mounting ball 208 within the reticulation cavity 220 of the socket 134. When the saw guide 26 has been properly positioned and pinned to the humerus 16 with pins extending through the pin holes 192, 194, 196 and into the humerus 16, the slotted cap 24 can be unscrewed from the socket 134. Once the slotted cap 24 is unscrewed from the socket 134, the mounting ball 208 can be removed from the cavity 156 of the socket 134 to decouple the saw guide 26 from the orientable holder 22 the sliding block 32 and the reamer clamp 30.

The mounting ball 208 is formed generally concentrically about a focus 222 located on the axis 214. Thus, the mounting ball 208 has a generally cylindrical outer surface 224 into which a zero positioning cavity 226 and a limiter cavity 228 are formed. The mounting ball 208 has an outside diameter 230 in areas where cavities 226, 228 are not formed. In the illustrated embodiment, the outside diameter 230 of the mounting ball 208 is approximately 0.36 inches. The outside diameter 230 of the mounting ball 208 is larger than the diameter 215 of the shaft 202 and the width 217 of the slot 216 formed in the slotted cap 24. Thus, when the mounting ball 208 is received in the cavity 156 and the slotted cap 24 is screwed into the internally threaded bore 218, the flat inner wall 298 of the slotted cap 24 acts to retain the mounting ball 208 in the reticulation cavity 220 of the socket 134.

The zero positioning cavity 226 is formed in the mounting ball 208 concentrically about a radial axis 232 extending perpendicular to the axis 214 in a plane perpendicular to the plane in which the captured saw blade slot 186 is formed.

The zero positioning cavity 226 has a diameter 234 slightly larger than, but approximately equal to, the diameter 236 of the end 238 of the shaft 240 of the zero positioning set screw 242 so that the end 238 of the zero positioning set screw 242 can be received therein to lock the saw guide 26 in a zero position.

The limiter cavity 228 is formed concentrically in the mounting ball 208 about a radial axis 244 extending perpendicular to the axis 214 in a plane perpendicular to the plane in which the captured saw blade slot 186 is formed. The limiter cavity 228 and the zero positioning cavity 226 are diametrically opposed on the mounting ball 208.

Figure 23:
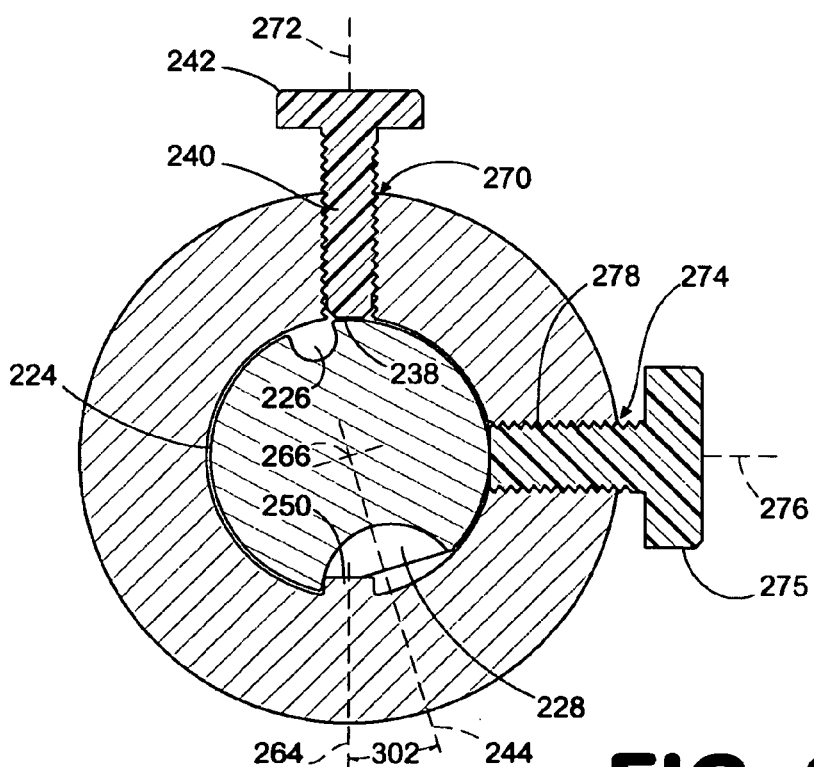
FIG. 23 is a view similar to that shown in FIG. 22 with the mounting ball rotated in one direction to its limit of adjustment established by the limiter peg engaging the wall of the limiter cavity.
Figure 24:
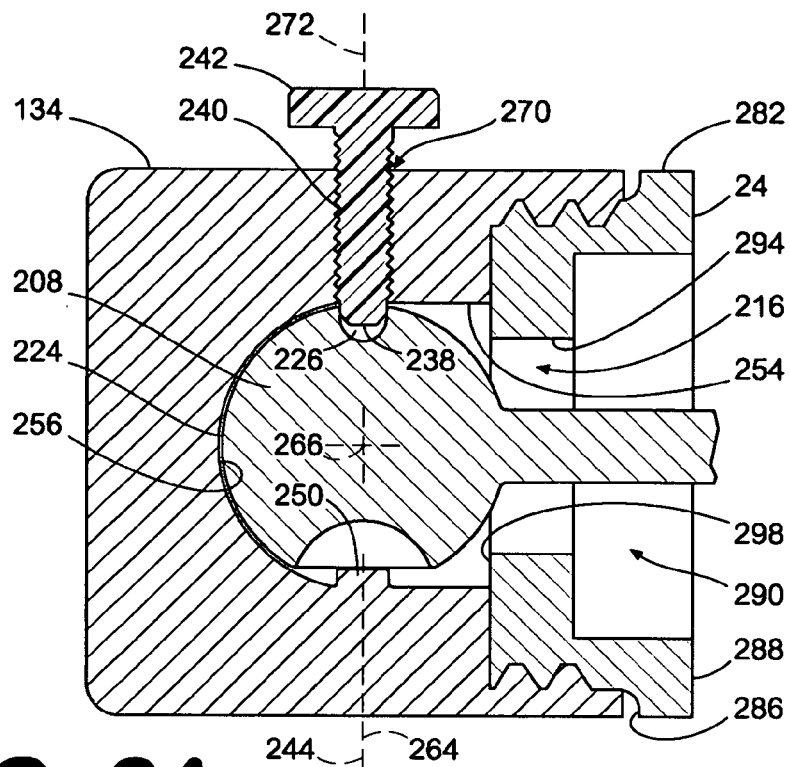
FIG. 24 is a sectional view taken through the plane of the axes of the zero positioning set screw and the socket of the mounting ball received in the cavity formed in the socket in a zero position established by the end of the shaft of the zero positioning set screw being received in the zero positioning cavity formed in the mounting ball.
Figure 25:
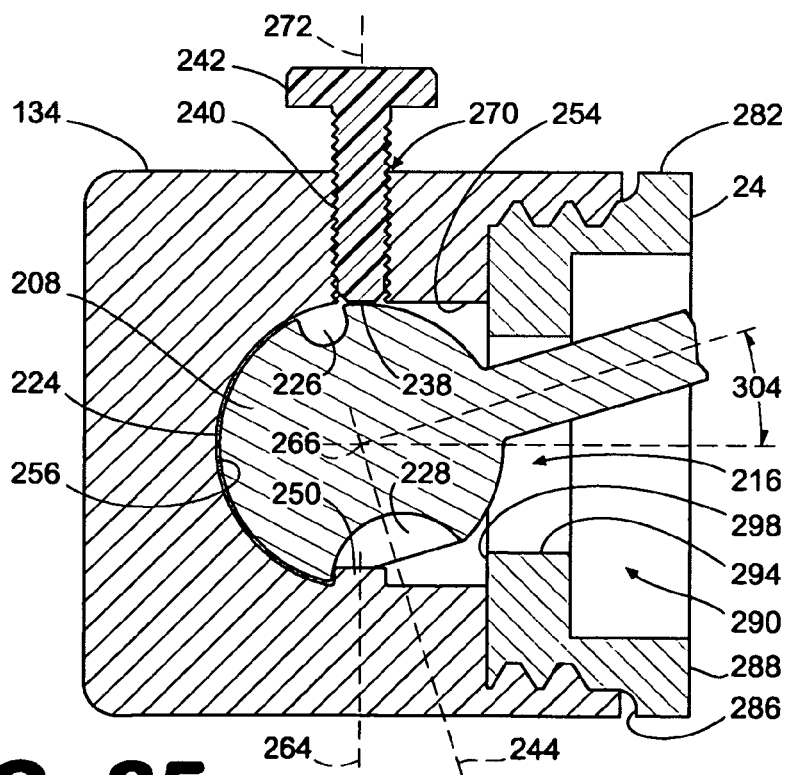
FIG. 25 is a view similar to that shown in FIG. 24 with the mounting ball rotated in one direction to its limit of adjustment established by the limiter peg engaging the wall of the limiter cavity.
Figure 26:
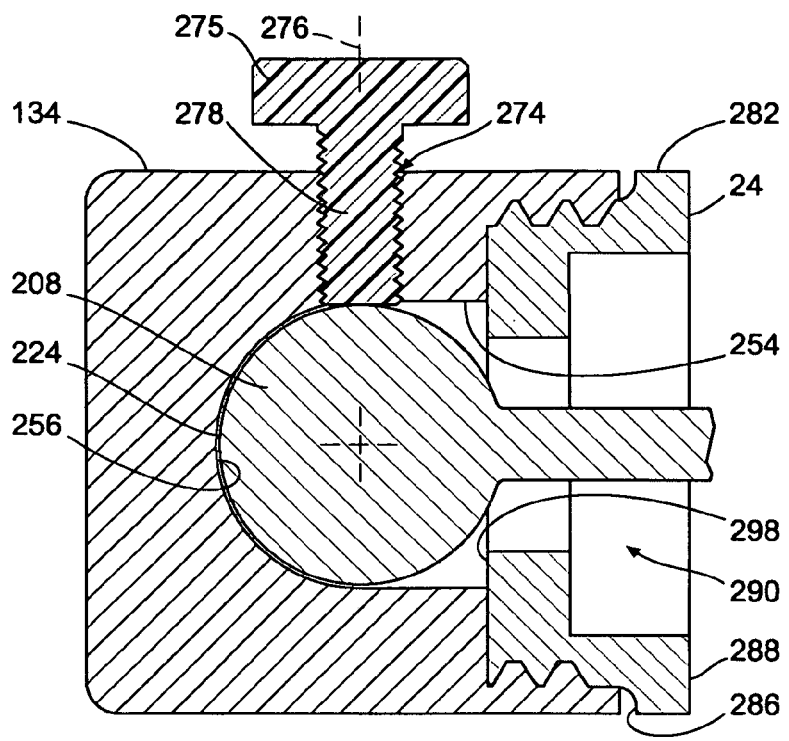
FIG. 26 is a sectional view taken through the plane of the axes of the socket and the orientation set screw of the mounting ball received in the cavity formed in the socket in a zero position.
Figure 27:
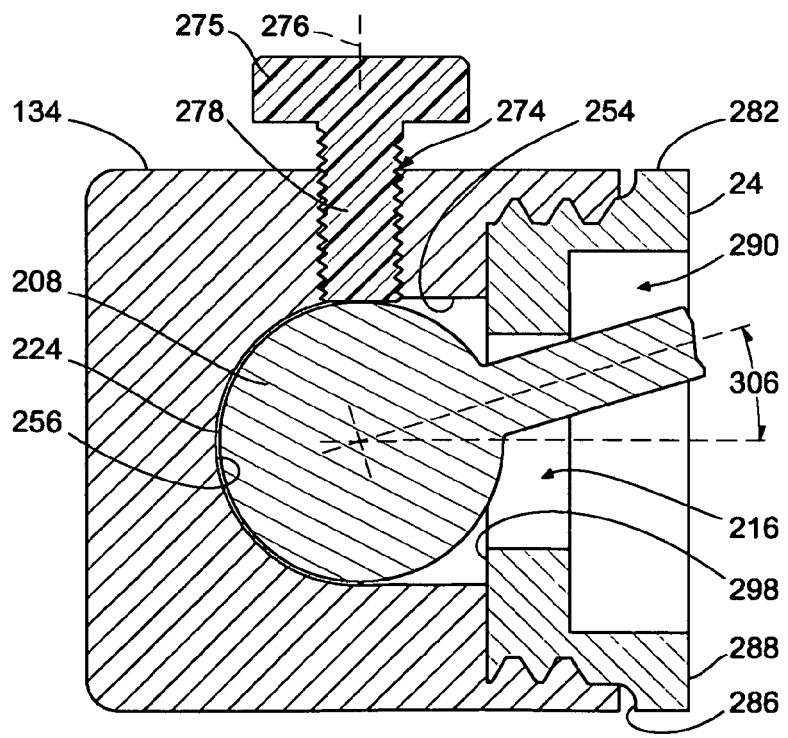
FIG. 27 is a view similar to that shown in FIG. 26 with the mounting ball rotated in one direction to its limit of adjustment established by the shaft of the coupling arm engaging the wall of the slot formed in the slotted cap.

The limiter cavity 228 has a radius of curvature 246 larger than the diameter 248 of a limiter peg 250 formed in the reticulation cavity 220 of the socket 134. In the illustrated embodiment, the radius of curvature 246 of the limiter cavity 228 is approximately 0.125 inches, while the diameter 248 of the limiter peg 250 is approximately 0.085 inches. Thus, the limiter cavity 228 is sized to be disposed over the limiter peg 250 while allowing a limited degree of rotation of the mounting ball 208 within the reticulation cavity 220. Thus, when the end 238 of the shaft 240 of the zero positioning set screw 242 is not received in the zero positioning cavity 226, the saw guide 26 can be adjusted within limits with respect to the socket 134 of the orientable holder 22. In the illustrated embodiment the limits of adjustment are approximately ±twenty degrees, as shown, by the angles 302, 304, 306 in FIGS. 23, 25 and 27.

As mentioned above, the socket 134 of the orientable holder 22 is detachably mounted to the saw guide 26. The cavity 156 of the socket 134 includes the reticulation cavity 220 and an internally threaded bore 218. The reticulation cavity 220 is sized and configured to receive the mounting ball 208 of the saw guide 26 therein. The internally threaded bore 218 is sized and threaded to receive the thread formed on the threaded shaft 284 of the slotted cap 24.

The mounting ball 208 of the saw guide 26 is detachably held in the reticulation cavity 220 until the captured saw blade slot 186 is properly oriented. The reticulation cavity 220 includes a cylindrical wall section 254 and a hemispherical wall section 256. The cylindrical wall section 254 has an inside diameter 258, which in the illustrated embodiment is approximately 0.365 inches. The radius of curvature 260 of the hemispherical wall 256 section is approximately 0.182 inches. The maximum displacement 262 of the hemispherical wall section 256 from the mounting end 154 of the socket 134 is, in the illustrated embodiment, is approximately 0.539 inches.

As previously mentioned, the socket 134 is formed to include the limiter peg 250 which extends inwardly at the junction of the cylindrical wall section 254 and the hemispherical wall section 256 of the reticulation cavity 220. The limiter peg 250 is formed concentrically about an axis 264 extending perpendicular to the axis 148 of the socket 134 and intersecting the axis 148 at the focus 266 of the radius of curvature of the hemispherical wall section 256. The axis 264 lies in a plane perpendicular to the plane of the captured saw blade slot 186 when the saw guide is in the zero position. The peg 250 has a height 268 that in the illustrated embodiment is approximately 0.042 inches. The dimensions of the limiter peg 250 and the limiter cavity 228 allow for about ±twenty degrees adjustment of the orientation of the cutting plane defined by the plates 180, 182 of the saw guide 26, as shown by angles 302, 304 in FIGS. 23 and 25.

A zero positioning screw hole 270 extends from the cylindrical side wall 152 through the socket 134 and the wall of the reticulation cavity 220. The zero positioning screw hole 270 is diametrically opposed to the limiter peg 250. Thus, the zero positioning screw hole 270 is formed concentrically about an axis 272 extending from the focus 266 of the radius of curvature of the hemispherical wall section 256 perpendicular to both the axis 148 of the socket 134 and the plane of the captured saw blade slot 186 when the saw guide 26 is in the zero position. The zero positioning screw hole 270 is threaded to receive the external threads on the shaft 240 of a zero positioning set screw 242.

The zero positioning cavity 226 in the mounting ball 208 is sized to receive the end 238 of the shaft 240 of the zero positioning screw 242. When the mounting ball 208 is oriented so that the end 238 of the shaft 240 of the zero positioning set screw 242 can be advanced into the zero positioning cavity 226, the set screw 242 and the cavity 226 cooperate to lock the saw guide 26 at one hundred thirty-five degrees of retroversion.

An orientation locking set screw hole 274 extends from the cylindrical side wall 152 through the socket 134 and the wall of the reticulation cavity 220. The orientation locking set screw hole 274 is formed concentrically about an axis 276 extending from the focus 266 of the radius of curvature of the hemispherical wall section 256 perpendicular to the axis 148 of the socket 134 and parallel to the plane of the captured saw blade slot 186 when the saw guide 26 is in the zero position. Thus, the orientation locking set screw hole 274 is disposed 90 degrees from both the zero positioning set screw hole 270 and the limiter peg 250. The orientation locking set screw hole 274 is threaded to receive the external thread formed on the shaft 278 of an orientation locking set screw 275. Regardless of whether or not the mounting ball 208 is oriented so that the end 238 of the shaft 240 of the zero positioning set screw 242 can be advanced into the zero positioning cavity 226, the orientation locking set screw 275 can be brought into engagement with the outer surface 224 of the mounting ball 208 to lock the saw guide 26 in any of the orientations permitted by the limiter peg 250 and the limiter cavity 228.

The slotted cap 24 includes an axis 280, a head 282, a threaded shaft 284 and a slot 216. The head 282 is formed concentrically about the axis 280. The threaded shaft 284 is also formed concentrically about the axis 280. The head 282 includes an inner wall 286, an outer wall 288 and a cavity 290 formed therein. The threaded shaft extends axially from the head 282.

The slot 216 extends radially inwardly from the head 282 and the shaft 284. The slot 216 is formed with a straight wall section 292 and a semicircular wall section 294. The straight wall section 292 has a width 217 which in the illustrated embodiment is 0.230 inches. The semicircular wall section 294 is formed about the axis 280 and has a radius 296 of approximately 0.115 inches. The threaded shaft 284 includes a flat inner wall 298 that is displaced from the inner wall 286 of the head 282 by a displacement 300 which in the illustrated embodiment is approximately 0.220 inches. When the threaded shaft 284 is screwed into the threaded bore 218 of the cavity 156 of the socket 134, the inner wall 298 of the shaft 284 retains the mounting ball 208 in the socket 134 and restricts the motion of the saw guide 26.

Figure 28:
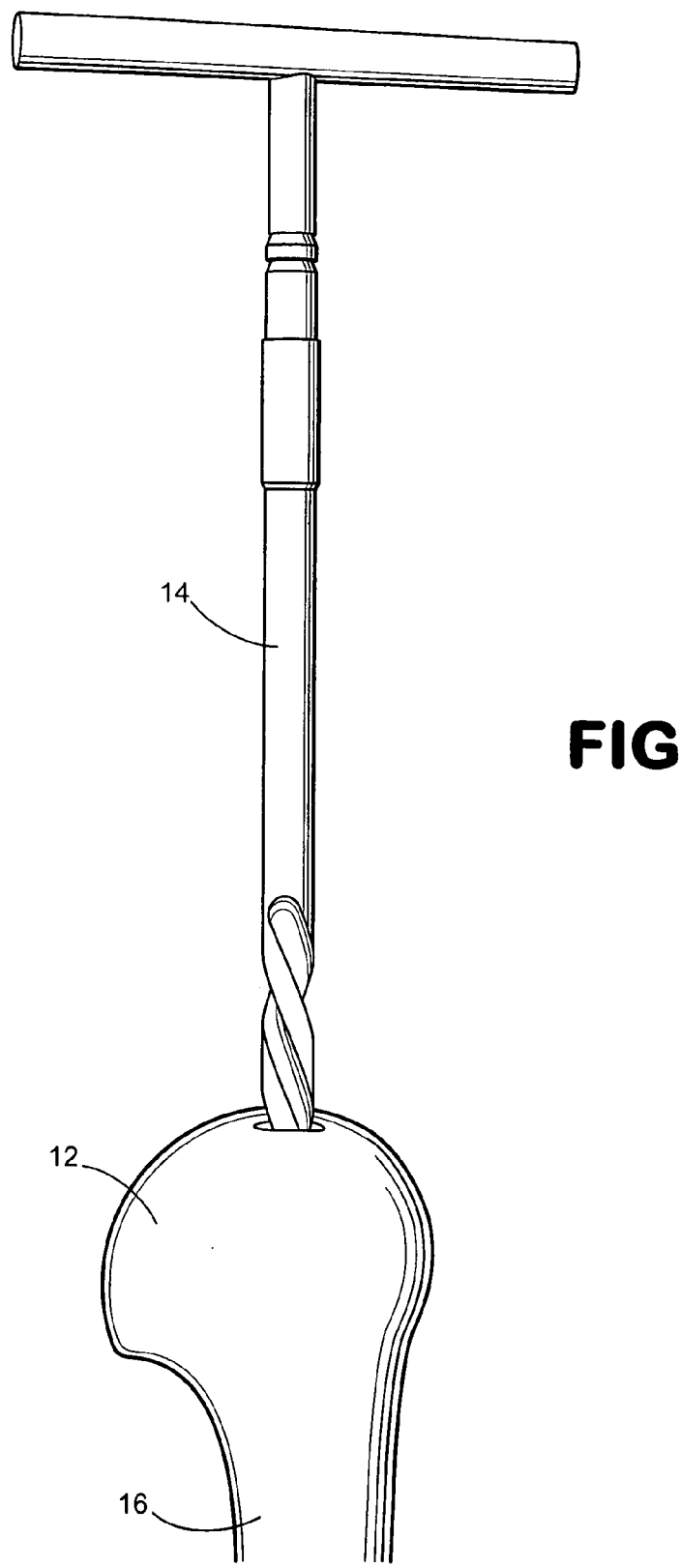
FIG. 28 is a perspective view of a T-handle attached to a reamer extending through the head of the humerus into the intramedullary canal as a step of preparing the humerus for receipt of a component of a prosthesis and as a step of resecting the humeral head.

The procedure for using the adjustable humeral cutting guide 10 includes the steps of reaming the intramedullary canal of the humerus 16 with a reamer 14 and leaving the reamer 14 in the canal to act as a positioning element as shown, for example, in FIG. 28. The reamer clamp assembly 20 is attached to the orientable holder 22 either before or after attaching the reamer clamp 30 to the reamer 14 positioned in the intramedullary canal of the humerus 16.

Figure 30:
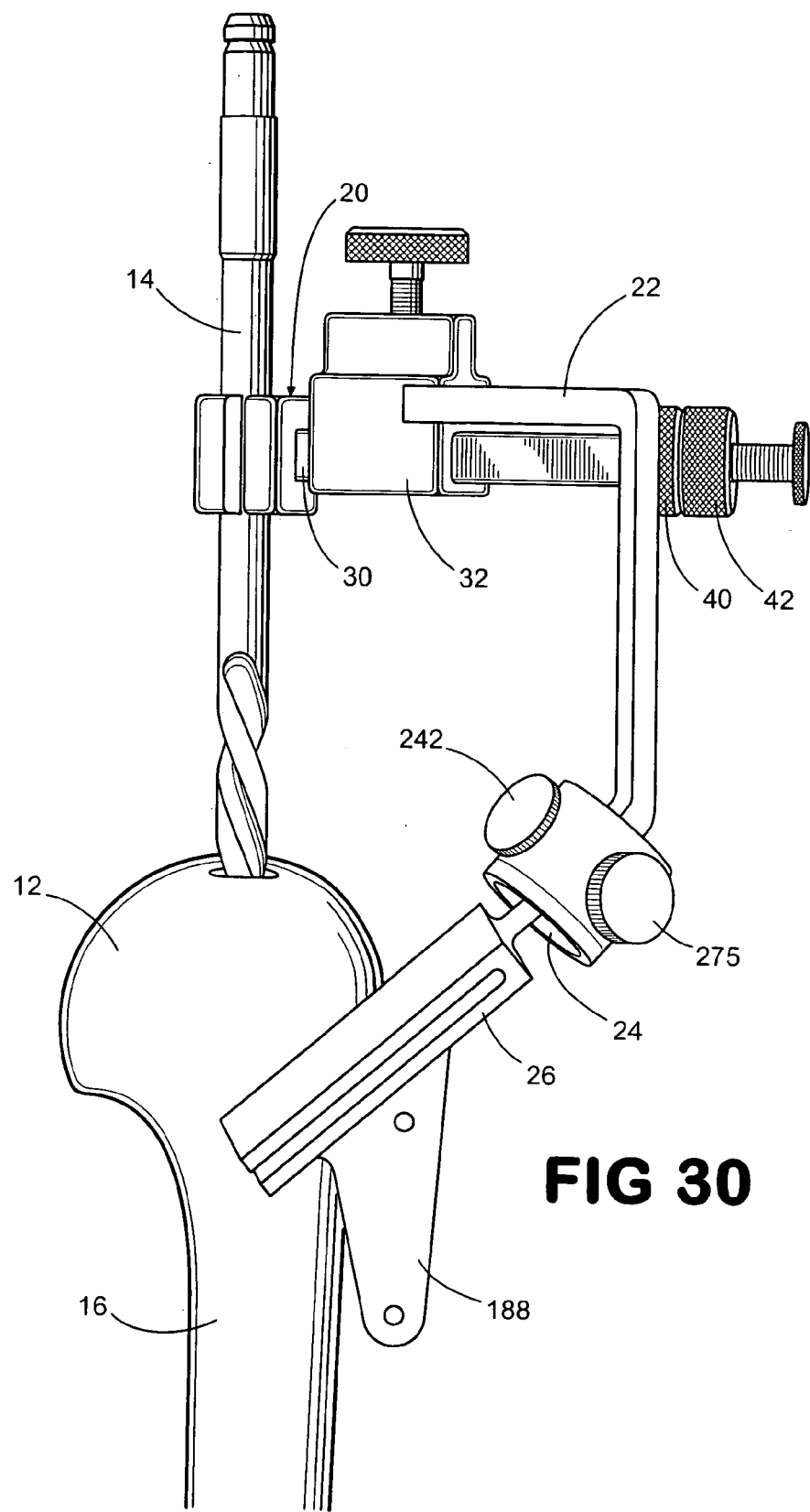
FIG. 30 is a perspective view similar to FIG. 29 with the clamp portion moved to a second location on the reamer, mounting arm of the orientable holder slightly inserted into the sliding block located at a different location on the clamp body and the saw guide locked in the zero position.

FIG. 29 shows the reamer clamp assembly 20 being attached to the reamer 14. FIG. 30 shows the orientable holder 22 and the saw guide 26 being attached to the reamer clamp assembly 20. The saw guide 26 is attached to the orientable holder 22 with the end 238 of the shaft 240 of the zero positioning set screw 242 received in the zero positioning cavity 226, as shown, for example, in FIG. 30. The reamer clamp 30 is moved on the reamer 14 to the correct height for the guide 10, compare FIGS. 30 and 31. The reamer clamp 30 is rotated about the reamer 14 if required and the sliding block 32 is moved along the reamer clamp 30 to approximately position the saw guide 26 in the appropriate anterior/posterior orientation.

If the captured saw blade slot 186 is appropriately oriented following the above steps, e.g. when a patient exhibits one hundred thirty-five degree retroversion, the orientation set screw is tightened to secure the saw guide 26 in the appropriate orientation. If the anatomy of the patient's humerus 16 is not conducive to being resected along the resecting plane that the captured saw blade slot 186 defines when locked in the zero position, the surgeon rotates the head of the zero positioning set screw 242 to back the end 238 of the shaft 240 out of the zero positioning cavity 226. The saw guide 26 is then free to be pivoted anteriorly/posteriorly and medially/laterally and to be rotated about the axis of the coupling arm 190 to position the captured saw blade slot 186 to define a suitable plane of reference for the resection of the humeral head. Once the desired resection plane is defined by the captured saw blade slot 186, the surgeon turns the head of the orientation set screw 275 to lock the mounting ball 208 in a fixed position relative to the socket 134. The surgeon may also tighten the zero positioning set screw 242 so that the end 238 engages the outer surface 224 of the mounting ball 208. Thus, the saw guide 26 has been locked in the proper varus/valgus angle through adjusting the saw guide 26 in three-dimensional space.

Figure 31:
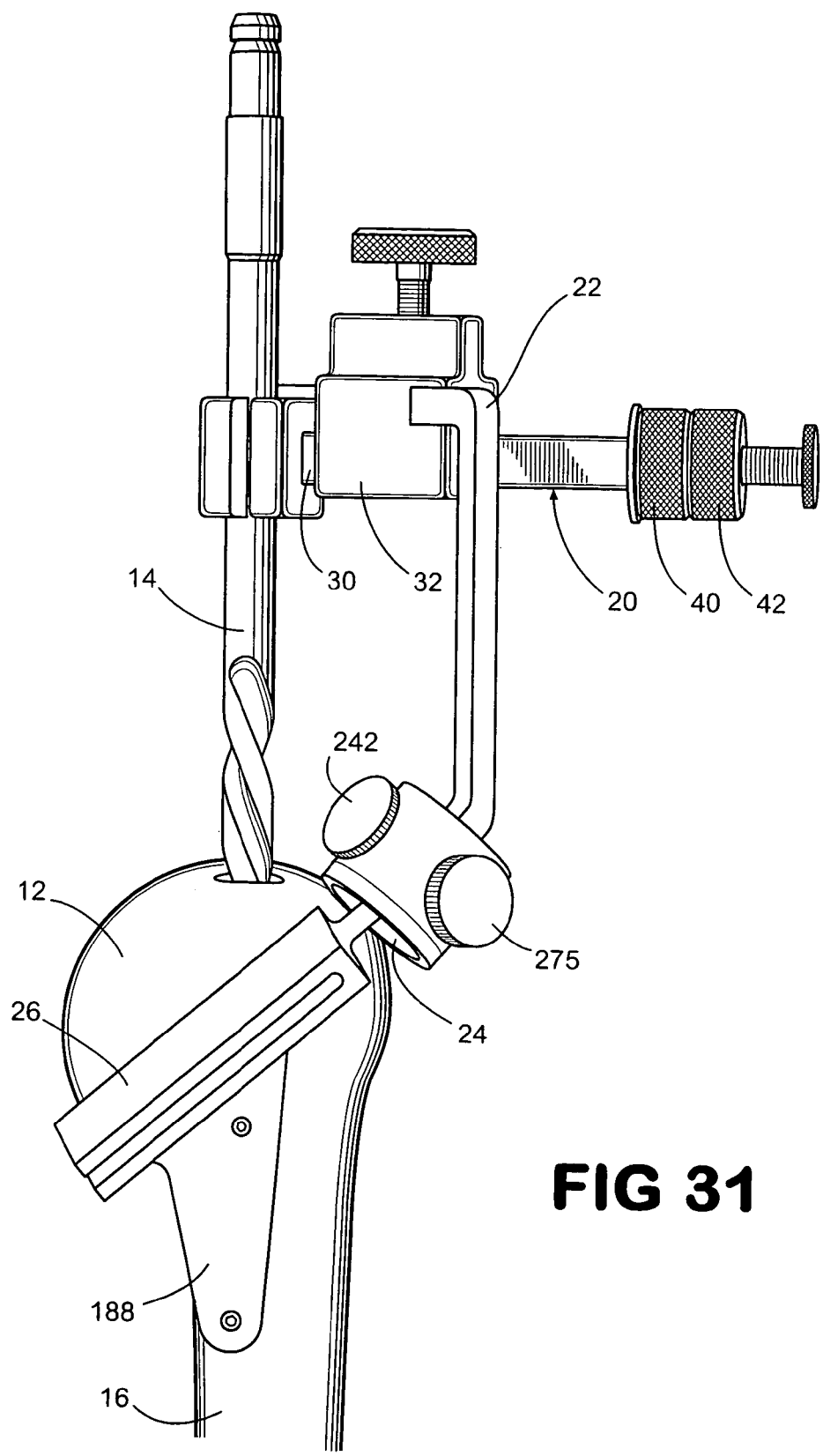
FIG. 31 is a perspective view similar to FIG. 30 with the saw guide adjusted to define a desired cutting plane for resection of the humeral head and pins inserted through the pin-receiving holes in the mounting plate to pin the saw guide to the humerous in the desired position.
Figure 32:
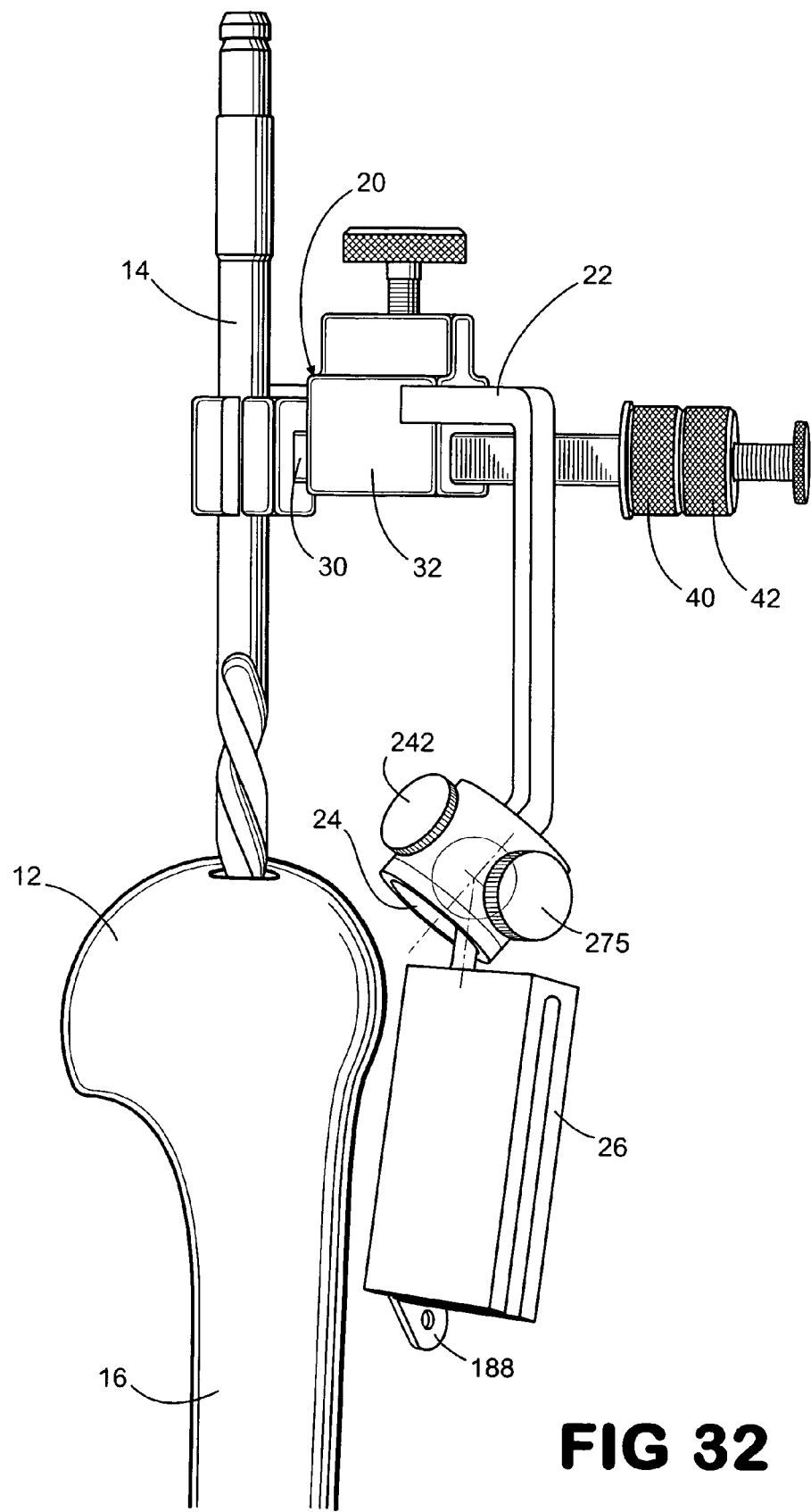
FIG. 32 is another perspective view of the adjustable humeral cutting guide pinned to the bone in the desired position.

While still locked in the proper orientation, three pins are then placed into the humerus through the pin holes 192, 194, 196 in the mounting plate 188 of the saw guide 26 to mount the saw guide 26 to the humerus 16, as shown, for example, in FIG. 31. The threaded slotted cap 24 and the set screws 242, 275, 164 connecting the saw guide 26 to the orientable holder 22, and the orientable holder 22 to the reamer clamp assembly 20 are loosened. The lock nuts 40, 42 are loosened and the jaws 50, 68 are spread apart so that the reamer clamp assembly 20 can be removed from the reamer 14. The reamer clamp assembly 20 is removed from the reamer 14 and the saw guide 26 is disconnected from the orientable holder 22. The reamer 14 is then taken out of the bone. Once other pieces of the adjustable cutting guide 10 are removed, the surgeon uses the captured saw blade slot 186 to guide a saw during resection of the humeral head. After the cut, the pins are removed from the humerus 16 and the saw guide 26 to permit the saw guide 26 to be unmounted from the humerus 16. The disclosed cutting guide 10 allows for a three-dimensional cutting plane to be obtained with a guide.

While the adjustable cutting guide 10 has been described and illustrated as being utilized to guide the resection of the humeral head, it is within the scope of the disclosure for the cutting guide 10 to be utilized for resecting other bones. Additionally, while the described adjustable cutting guide 10 has been described as being clamped to a reamer received in the intramedullary canal of a bone, it is within the scope of the disclosure for the adjustable cutting guide to be coupled to some other positioning structure or intramedullary alignment member by means other than clamping using an alternative extramedullary alignment member and translatable member other than reamer clamp 30 and sliding block 32. The reamer 14 acts as a convenient and conventional site for the temporary attachment of saw guides, but other tools and pins and even bone structure may serve as a positioning structure. For instance, it is possible that a threaded rod could be inserted into the intramedullary canal to act as an intramedullary alignment member, or positioning structure, and that an extramedullary member including an appropriately tapped hole could be screwed onto the threaded rod.

Also, it is within the scope of the disclosure to temporarily couple the saw guide 26 and orientable holder 22 to the positioning guide with other linkages and for the configuration of the saw guide and orientable holder to differ from that shown and described herein. For instance, it would be within the scope of the disclosure for the saw guide to be formed to include a socket 134 and the orientable holder to be formed to include a mounting ball 208 or for the mounting ball 208 or socket 134 to be formed on some other linkage member to form an orientable coupling.

Although specific embodiments of the invention have been described herein, other embodiments may be perceived by those skilled in the art without departing from the scope of the invention as defined by the following claims. For example, although the invention has been described in terms of the resection of a humeral head, it can be used with prostheses for other joints such as the hip, knee, or elbow.

What is claimed is:

1. An adjustable cutting guide for defining a cutting plane for a saw in a bone, the cutting guide comprising:
    a clamp configured to be secured to a positioning structure;
    a saw guide with a slot therein, the slot formed to cooperate with a saw to limit the saw to cutting in a specific plane;
    an orientable coupling mounted to the clamp and the saw guide,
    wherein the orientable coupling comprises a first coupling component and a second coupling component,
    wherein one of the first coupling component and second coupling component is coupled to the saw guide and the other of the first coupling component and second coupling component is coupled to the clamp,
    wherein the first coupling component includes a partially spherical shaped portion,
    wherein the second coupling component includes a socket member defining a partially spherical shaped concave surface configured to receive the partially spherical shaped portion, and
    wherein the first coupling component articulates in relation to the second coupling component in a ball and socket fashion; and
    a limiter for limiting articulation of the first coupling component in relation to the second coupling component,
    wherein the limiter includes (i) a peg formed in one of the first coupling component and second coupling component and (ii) a cavity sized to receive the peg formed in the other of the first coupling component and the second coupling component.

2. The apparatus of claim 1 wherein the clamp is configured to be adjusted in a horizontal direction relative to the positioning structure, when the positioning structure extends horizontally from the bone, prior to being secured to the positioning structure.

3. The apparatus of claim 2 wherein the clamp is configured to permit the clamp to be pivotally adjusted about the positioning structure in a plane transverse to the horizontal direction prior to being secured to the positioning structure.

4. The apparatus of claim 2 wherein the clamp includes an axis transverse to the horizontal direction and the orientable coupling is configured to be mounted to the clamp at various axial positions relative to the axis.

5. The apparatus of claim 1 wherein the orientable coupling is configured to facilitate decoupling of the saw guide from the clamp.

6. The apparatus of claim 5 wherein the saw guide is formed to include mounting structure facilitating mounting the saw guide to the bone prior to the saw guide being decoupled from the clamp.

7. An adjustable cutting guide for resection of a bone comprising:
    a positioning structure configured to be at least temporarily fixed relative to the bone;
    a clamp adapted to be coupled to the positioning structure for movement longitudinally with respect to a longitudinal axis of the bone and radially about the longitudinal axis of the bone;
    a member coupled to the clamp for movement relative to the clamp in a direction transverse to the longitudinal axis of the bone;
    a saw guide defining a resection plane of reference for a saw received therein;
    an orientable coupling extending between the saw guide and member,
    wherein the orientable coupling comprises a first coupling component and a second coupling component,
    wherein one of the first coupling component and second coupling component is coupled to the saw guide and the other of the first coupling component and second coupling component is coupled to the clamp,
    wherein the first coupling component includes a partially spherical shaped portion,
    wherein the second coupling component includes a socket member defining a partially spherical shaped concave surface configured to receive the partially spherical shaped portion, and
    wherein the first coupling component articulates in relation to the second coupling component in a ball and socket fashion; and
    a limiter for limiting articulation of the first coupling component in relation to the second coupling component,
    wherein the limiter includes (i) a peg formed in one of the first coupling component and second coupling component and (ii) a cavity sized to receive the peg formed in the other of the first coupling component and the second coupling component.

8. The apparatus of claim 7 wherein the clamp and positioning structure are configured to permit the clamp to be pivotally adjusted about the positioning structure in a plane transverse to a horizontal direction prior to being secured to the positioning structure, wherein said horizontal direction is normal to the longitudinal axis.

9. The apparatus of claim 8 wherein the clamp includes an axis transverse to the horizontal direction and the orientable coupling is configured to be mounted to the member at various axial positions relative to the axis.

10. The apparatus of claim 7 wherein the orientable coupling is configured to facilitate decoupling of the saw guide from the clamp.

11. An apparatus for guiding the resection of the head of a humerus comprising:

an intramedullary alignment member having a longitudinal axis and being structured for substantial axial alignment with the intramedullary canal of a humerus;

an extramedullary alignment member, extending substantially perpendicularly from said intramedullary alignment member and being translatable along and rotatable about the longitudinal axis of the intramedullary alignment member;

a translatable member translatable along the extramedullary alignment member;

a saw guide including a slot configured to restrict the orientation of a saw to define a plane when the saw is received therein; and an orientable coupling extending between the saw guide and the translatable member and being configured to translate with respect to the translatable member in a direction transverse to the extramedullary alignment member and being configured to orient the slot of the saw guide in an orientation relative to the head of the humerus within a range desirable for humeral resection through at least anterior/posterior and medial/lateral adjustment plane defined by the slot.

12. The apparatus of claim 11 wherein the orientable coupling comprises a first portion and a second portion, the first portion including a ball and the second portion including a socket sized to receive the ball for reticulation therein and wherein one of the first portion and second portion is coupled to the saw guide and the other of the first portion and second portion is coupled to the translatable member.

13. The apparatus of claim 12 and further comprising a limiter for limiting the reticulation of the ball relative to the socket.

14. The apparatus of claim 13 wherein the limiter includes a peg formed in one of the ball and the socket and a cavity sized to receive the peg formed in the other of the ball and the socket.

15. A method of resecting a bone having a longitudinal axis at a site for receipt of a prosthesis comprising the steps of:

attaching a positioning structure to the bone adjacent the site, the positioning structure extending longitudinally from the bone;

providing a saw guide having a saw receiving aperture defining a resecting plane for a saw received therein, said saw guide being configured for removable coupling to the positioning structure and for adjusting the saw-receiving aperture longitudinally, anteriorly/posteriorly and medially/laterally with respect to the bone;

securing the saw guide to the positioning structure at a desired longitudinal position relative to the bone;

adjusting the saw guide to align the resecting plane with a desired plane of resection of the bone;

removably affixing the saw guide to the bone following the adjusting step and prior to resecting the bone along the desired plane;

removing the saw guide from the positioning structure following the removably affixing step and prior to resecting the bone along the desired plane;

detatching the positioning structure from the bone prior to resecting the bone along the desired plane; and resecting the bone along the desired resection plane by moving a cutting surface of a saw in the resecting plane while the saw is received in the saw receiving aperture, wherein the attaching step includes reaming the intramedullary canal of the bone with a reamer and leaving the reamer in the intramedullary canal to act as the positioning structure throughout the securing, adjusting and removably affixing steps, and wherein the provided saw guide includes a coupling component configured for coupling to the positioning element and which is adjustable relative to the positioning structure longitudinally and radially about the longitudinal axis of the bone, a guide component including the saw receiving aperture and a mounting structure configured to permit the guide component to be removably affixed to the bone and a coupling removably coupling the guide component to the coupling component and configured to permit the guide component to be adjusted anteriorly and posteriorly and medially and laterally with respect to the bone and further comprising the steps of coupling the guide component to the coupling component prior to the adjusting step and decoupling the guide component from the coupling component following the removably affixing step and prior to the resecting step.

16. The method of claim 15 wherein the adjusting step includes adjusting the saw guide to align the anterior/posterior angle and medial/lateral angle of the resecting plane.

17. The method of claim 16 wherein the adjusting step includes rotating the saw guide secured to the reamer about the longitudinal axis of the bone.

* * * * *